(12) United States Patent
Viscardi et al.

(10) Patent No.: US 8,906,102 B2
(45) Date of Patent: *Dec. 9, 2014

(54) LATERAL ENTRY INSERT FOR CUP TRIAL

(71) Applicant: Howmedica Osteonics Corp., Mahwah, NJ (US)

(72) Inventors: David Viscardi, Hoboken, NJ (US); Koustubh Rao, Hackensack, NJ (US); Shawn Michael Kroll, Waldwick, NJ (US); Roy Splieth, Central Valley, NY (US); James David Lorek, Cary, NC (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/767,074

(22) Filed: Feb. 14, 2013

(65) Prior Publication Data

US 2013/0325134 A1    Dec. 5, 2013

Related U.S. Application Data

(63) Continuation-in-part of application No. 13/484,557, filed on May 31, 2012, now Pat. No. 8,663,334.

(51) Int. Cl.
*A61F 2/40* (2006.01)
*A61F 2/30* (2006.01)
*A61F 2/46* (2006.01)

(52) U.S. Cl.
CPC .............. *A61F 2/4014* (2013.01); *A61F 2/4684* (2013.01); *A61F 2002/4022* (2013.01); *A61F 2002/4037* (2013.01); *A61F 2002/4044* (2013.01)
USPC ..................................... 623/19.11; 623/23.43

(58) Field of Classification Search
CPC ........ A61F 2/4684; A61F 2/40; A61F 2/4014; A61F 2/4059; A61F 2/4081; A61F 4/4607; A61F 2/4612
USPC ............... 623/19.11–19.14, 23.29–23.47, 623/22.4–22.46, 23.11
See application file for complete search history.

(56) References Cited

U.S. PATENT DOCUMENTS 3,102,536 A    9/1963  Rose
3,806,957 A    4/1974  Shersher et al.
(Continued)

FOREIGN PATENT DOCUMENTS

DE          10335442 A1     2/2005
DE     202008008565 U1     8/2008
(Continued)

OTHER PUBLICATIONS

Extended European Search Report for Application No. EP12195588 dated Mar. 1, 2013.

(Continued)

*Primary Examiner* — Alvin Stewart
(74) *Attorney, Agent, or Firm* — Lerner, David, Littenberg, Krumholz & Mentlik, LLP

(57) ABSTRACT

Trials for a reverse shoulder system are described. The trials generally include an insert housed within a humeral cup. The insert has a proximal end and a distal end, the proximal end having a concave recess therein adapted to receive a glenosphere prosthesis. The distal end of the insert includes a shaft, the shaft is substantially housed within the confines of the humeral cup. A distal end of the humeral cup is inserted in a humeral stem.

20 Claims, 19 Drawing Sheets

(56) References Cited

U.S. PATENT DOCUMENTS

| | | | |
|---|---|---|---|
| 3,842,442 A | 10/1974 | Kolbel | |
| 3,978,528 A | 9/1976 | Crep | |
| 4,030,143 A | 6/1977 | Elloy et al. | |
| 4,040,131 A | 8/1977 | Gristina | |
| 4,279,041 A | 7/1981 | Buchholz et al. | |
| 4,524,467 A | 6/1985 | DeCarlo, Jr. | |
| D285,968 S | 9/1986 | Kinnett | |
| 4,693,723 A | 9/1987 | Gabard et al. | |
| 4,711,639 A | 12/1987 | Grundei | |
| 4,795,468 A | 1/1989 | Hodorek et al. | |
| 4,936,853 A | 6/1990 | Fabian et al. | |
| 4,944,757 A | 7/1990 | Martinez et al. | |
| 5,080,673 A | 1/1992 | Burkhead et al. | |
| 5,358,526 A * | 10/1994 | Tornier | 623/19.14 |
| 5,413,604 A | 5/1995 | Hodge | |
| 5,462,563 A | 10/1995 | Shearer et al. | |
| 5,489,309 A * | 2/1996 | Lackey et al. | 623/19.14 |
| 5,569,263 A | 10/1996 | Hein | |
| 5,609,639 A | 3/1997 | Walker et al. | |
| 5,609,644 A | 3/1997 | Ashby et al. | |
| 5,658,340 A | 8/1997 | Muller et al. | |
| 5,702,447 A | 12/1997 | Walch et al. | |
| 5,702,457 A | 12/1997 | Walch et al. | |
| 5,702,470 A | 12/1997 | Menon | |
| 5,702,486 A * | 12/1997 | Craig et al. | 623/19.14 |
| 5,723,018 A * | 3/1998 | Cyprien et al. | 623/19.13 |
| 5,728,161 A | 3/1998 | Camino et al. | |
| 5,741,335 A * | 4/1998 | Gerber et al. | 623/19.13 |
| 5,755,801 A | 5/1998 | Walker et al. | |
| 5,824,106 A | 10/1998 | Fournol | |
| 5,871,545 A | 2/1999 | Goodfellow et al. | |
| 5,879,401 A | 3/1999 | Besemer et al. | |
| 5,910,171 A | 6/1999 | Kummer et al. | |
| 5,961,555 A * | 10/1999 | Huebner | 623/19.11 |
| 5,964,808 A | 10/1999 | Blaha et al. | |
| 6,015,437 A * | 1/2000 | Stossel | 623/19.11 |
| 6,033,439 A * | 3/2000 | Camino et al. | 623/19.11 |
| 6,045,582 A * | 4/2000 | Prybyla | 623/19.11 |
| 6,102,953 A | 8/2000 | Huebner | |
| 6,120,542 A * | 9/2000 | Camino et al. | 623/19.11 |
| 6,123,728 A | 9/2000 | Brosnahan et al. | |
| 6,129,764 A * | 10/2000 | Servidio | 623/19.11 |
| 6,168,627 B1 | 1/2001 | Huebner | |
| 6,168,628 B1 | 1/2001 | Huebner | |
| 6,193,758 B1 * | 2/2001 | Huebner | 623/19.14 |
| 6,197,062 B1 * | 3/2001 | Fenlin | 623/19.12 |
| 6,197,063 B1 * | 3/2001 | Dews | 623/19.14 |
| 6,206,925 B1 | 3/2001 | Tornier | |
| 6,210,444 B1 | 4/2001 | Webster et al. | |
| 6,217,618 B1 | 4/2001 | Hileman | |
| 6,228,119 B1 * | 5/2001 | Ondrla et al. | 623/19.11 |
| 6,228,120 B1 * | 5/2001 | Leonard et al. | 623/19.12 |
| 6,283,999 B1 * | 9/2001 | Rockwood, Jr. | 623/19.12 |
| 6,368,352 B1 | 4/2002 | Camino et al. | |
| 6,379,388 B1 | 4/2002 | Ensign et al. | |
| 6,485,520 B1 | 11/2002 | Hubach et al. | |
| 6,494,913 B1 | 12/2002 | Huebner | |
| 6,500,208 B1 | 12/2002 | Metzger et al. | |
| 6,508,840 B1 * | 1/2003 | Rockwood et al. | 623/19.12 |
| 6,508,841 B2 | 1/2003 | Martin et al. | |
| 6,514,287 B2 * | 2/2003 | Ondrla et al. | 623/19.13 |
| 6,520,994 B2 * | 2/2003 | Nogarin | 623/19.14 |
| 6,524,342 B1 * | 2/2003 | Muhlhausler et al. | 623/19.14 |
| 6,530,957 B1 * | 3/2003 | Jack | 623/19.14 |
| 6,569,202 B2 | 5/2003 | Whiteside | |
| 6,589,282 B2 * | 7/2003 | Pearl | 623/19.14 |
| 6,602,292 B2 | 8/2003 | Burkinshaw | |
| 6,673,114 B2 * | 1/2004 | Hartdegen et al. | 623/19.12 |
| 6,679,916 B1 | 1/2004 | Frankle et al. | |
| 6,719,799 B1 * | 4/2004 | Kropf | 623/19.14 |
| 6,736,852 B2 * | 5/2004 | Callaway et al. | 623/19.14 |
| 6,749,637 B1 * | 6/2004 | Bahler | 623/19.14 |
| 6,761,740 B2 | 7/2004 | Tornier | |
| 6,790,234 B1 * | 9/2004 | Frankle | 623/19.12 |
| 6,800,094 B2 | 10/2004 | Burkinshaw | |
| 6,818,019 B2 * | 11/2004 | Horber | 623/18.11 |
| 6,887,276 B2 * | 5/2005 | Gerbec et al. | 623/18.11 |
| 6,887,277 B2 * | 5/2005 | Rauscher et al. | 623/19.13 |
| 6,890,358 B2 | 5/2005 | Ball et al. | |
| 6,899,736 B1 | 5/2005 | Rauscher et al. | |
| 6,942,699 B2 * | 9/2005 | Stone et al. | 623/19.14 |
| 6,953,478 B2 | 10/2005 | Bouttens et al. | |
| 6,969,406 B2 | 11/2005 | Tornier et al. | |
| 6,969,407 B2 | 11/2005 | Klotz et al. | |
| 6,986,790 B2 * | 1/2006 | Ball et al. | 623/19.11 |
| 6,986,791 B1 | 1/2006 | Metzger | |
| 7,011,686 B2 * | 3/2006 | Ball et al. | 623/19.14 |
| 7,033,396 B2 * | 4/2006 | Tornier | 623/19.11 |
| 7,044,973 B2 * | 5/2006 | Rockwood et al. | 623/19.12 |
| 7,097,663 B1 * | 8/2006 | Nicol et al. | 623/19.13 |
| 7,108,405 B2 | 9/2006 | Matts et al. | |
| 7,108,719 B2 * | 9/2006 | Horber | 623/19.11 |
| 7,166,132 B2 * | 1/2007 | Callaway et al. | 623/23.47 |
| 7,169,184 B2 * | 1/2007 | Dalla Pria | 623/19.12 |
| 7,175,663 B1 * | 2/2007 | Stone | 623/19.13 |
| 7,175,664 B1 * | 2/2007 | Lakin | 623/19.14 |
| 7,186,269 B2 * | 3/2007 | Cyprien et al. | 623/19.11 |
| 7,204,854 B2 | 4/2007 | Guederian et al. | |
| 7,238,207 B2 * | 7/2007 | Blatter et al. | 623/19.14 |
| 7,238,208 B2 | 7/2007 | Camino et al. | |
| 7,241,314 B1 | 7/2007 | Winslow | |
| 7,297,163 B2 | 11/2007 | Huebner | |
| 7,303,585 B2 * | 12/2007 | Horber | 623/19.14 |
| 7,309,360 B2 | 12/2007 | Tornier et al. | |
| 7,329,284 B2 | 2/2008 | Maroney et al. | |
| 7,338,528 B2 * | 3/2008 | Stone et al. | 623/19.14 |
| 7,357,817 B2 | 4/2008 | D'Alessio, II | |
| 7,425,214 B1 | 9/2008 | McCarthy et al. | |
| 7,445,638 B2 | 11/2008 | Beguin et al. | |
| 7,462,197 B2 | 12/2008 | Tornier et al. | |
| 7,465,319 B2 * | 12/2008 | Tornier | 623/19.11 |
| 7,470,287 B2 * | 12/2008 | Tornier et al. | 623/19.13 |
| 7,531,003 B2 | 5/2009 | Reindel | |
| 7,537,618 B2 * | 5/2009 | Collazo | 623/19.14 |
| 7,544,211 B2 | 6/2009 | Rochetin | |
| 7,608,109 B2 * | 10/2009 | Dalla Pria | 623/19.11 |
| 7,611,539 B2 * | 11/2009 | Bouttens et al. | 623/19.11 |
| 7,621,961 B2 * | 11/2009 | Stone | 623/19.12 |
| 7,648,530 B2 * | 1/2010 | Habermeyer et al. | 623/19.11 |
| 7,678,150 B2 * | 3/2010 | Tornier et al. | 623/19.13 |
| 7,753,959 B2 * | 7/2010 | Berelsman et al. | 623/19.11 |
| 7,758,650 B2 * | 7/2010 | Dews et al. | 623/19.14 |
| 7,785,370 B2 * | 8/2010 | Collazo | 623/19.14 |
| 7,819,923 B2 * | 10/2010 | Stone et al. | 623/19.14 |
| 7,854,768 B2 * | 12/2010 | Wiley et al. | 623/19.14 |
| 7,918,892 B2 | 4/2011 | Huebner | |
| 7,922,769 B2 | 4/2011 | Deffenbaugh et al. | |
| 7,951,204 B2 | 5/2011 | Chambat et al. | |
| 7,959,680 B2 | 6/2011 | Stone et al. | |
| 8,002,838 B2 * | 8/2011 | Klotz | 623/19.14 |
| 8,002,841 B2 | 8/2011 | Hasselman | |
| 8,062,376 B2 * | 11/2011 | Shultz et al. | 623/19.13 |
| 8,070,820 B2 * | 12/2011 | Winslow et al. | 623/19.13 |
| 8,092,466 B2 * | 1/2012 | Splieth et al. | 606/102 |
| 8,105,385 B2 * | 1/2012 | Maroney et al. | 623/19.14 |
| 8,118,875 B2 * | 2/2012 | Rollet | 623/19.12 |
| 8,118,876 B2 | 2/2012 | Gupta et al. | |
| 8,137,407 B2 | 3/2012 | Todd et al. | |
| 8,142,510 B2 | 3/2012 | Lee et al. | |
| 8,147,557 B2 | 4/2012 | Lee et al. | |
| 8,147,558 B2 | 4/2012 | Lee et al. | |
| 8,157,866 B2 | 4/2012 | Winslow et al. | |
| 8,182,542 B2 * | 5/2012 | Ferko | 623/19.14 |
| 8,192,497 B2 * | 6/2012 | Ondrla | 623/19.14 |
| 8,206,453 B2 | 6/2012 | Cooney, III et al. | |
| 8,231,682 B2 * | 7/2012 | Lafosse et al. | 623/19.11 |
| 8,231,683 B2 | 7/2012 | Lappin et al. | |
| 8,236,059 B2 * | 8/2012 | Stone et al. | 623/19.14 |
| 8,241,366 B2 * | 8/2012 | Roche et al. | 623/19.13 |
| 8,246,687 B2 * | 8/2012 | Katrana et al. | 623/19.13 |
| 8,257,363 B2 * | 9/2012 | Splieth et al. | 606/102 |
| 8,273,130 B2 * | 9/2012 | Gradl | 623/18.12 |
| 8,277,511 B2 * | 10/2012 | Tornier et al. | 623/18.11 |
| 8,303,665 B2 * | 11/2012 | Tornier et al. | 623/19.11 |

(56) References Cited

U.S. PATENT DOCUMENTS

| | | | |
|---|---|---|---|
| 8,323,347 B2* | 12/2012 | Guederian et al. | 623/19.12 |
| 8,328,874 B2 | 12/2012 | Lee | |
| 8,337,563 B2* | 12/2012 | Roche et al. | 623/19.13 |
| 8,343,226 B2* | 1/2013 | Nogarin et al. | 623/19.13 |
| 8,361,157 B2 | 1/2013 | Bouttens et al. | |
| 8,366,780 B2 | 2/2013 | Klawitter et al. | |
| 8,377,142 B2 | 2/2013 | Trail et al. | |
| 8,419,798 B2* | 4/2013 | Ondrla et al. | 623/19.12 |
| 8,444,698 B2* | 5/2013 | Klotz et al. | 623/19.12 |
| 8,454,702 B2* | 6/2013 | Smits et al. | 623/19.11 |
| 8,460,390 B2* | 6/2013 | Biss et al. | 623/19.14 |
| 8,545,504 B2* | 10/2013 | Durand-Allen et al. | 606/86 R |
| 8,545,511 B2* | 10/2013 | Splieth et al. | 606/102 |
| 8,562,686 B2* | 10/2013 | Klotz et al. | 623/19.12 |
| 8,591,591 B2* | 11/2013 | Winslow et al. | 623/19.11 |
| 8,608,805 B2* | 12/2013 | Forrer et al. | 623/19.12 |
| 8,617,249 B2* | 12/2013 | Emami | 623/19.14 |
| 8,623,092 B2* | 1/2014 | Bickley et al. | 623/18.11 |
| 8,623,093 B2* | 1/2014 | Dickerson | 623/22.42 |
| 8,632,603 B2* | 1/2014 | Hodorek et al. | 623/23.27 |
| 8,647,387 B2* | 2/2014 | Winslow | 623/19.14 |
| 2001/0007957 A1 | 7/2001 | Martin et al. | |
| 2001/0011192 A1* | 8/2001 | Ondrla et al. | 623/19.13 |
| 2001/0011193 A1* | 8/2001 | Nogarin | 623/19.14 |
| 2001/0049561 A1* | 12/2001 | Dews et al. | 623/19.14 |
| 2001/0053935 A1* | 12/2001 | Hartdegen et al. | 623/19.12 |
| 2002/0016634 A1* | 2/2002 | Maroney et al. | 623/19.14 |
| 2002/0099445 A1* | 7/2002 | Maroney et al. | 623/19.14 |
| 2002/0120339 A1 | 8/2002 | Callaway et al. | |
| 2002/0128719 A1 | 9/2002 | Burkinshaw | |
| 2003/0014119 A1 | 1/2003 | Capon et al. | |
| 2003/0028253 A1* | 2/2003 | Stone et al. | 623/19.14 |
| 2003/0099519 A1 | 5/2003 | Robinson et al. | |
| 2003/0114933 A1 | 6/2003 | Bouttens et al. | |
| 2003/0149486 A1 | 8/2003 | Huebner | |
| 2003/0158605 A1 | 8/2003 | Tornier | |
| 2004/0030394 A1* | 2/2004 | Horber | 623/18.11 |
| 2004/0030396 A1* | 2/2004 | Horber | 623/19.12 |
| 2004/0039449 A1* | 2/2004 | Tornier | 623/19.13 |
| 2004/0059424 A1* | 3/2004 | Guederian et al. | 623/19.11 |
| 2004/0064187 A1* | 4/2004 | Ball et al. | 623/19.12 |
| 2004/0064188 A1* | 4/2004 | Ball et al. | 623/19.11 |
| 2004/0064190 A1* | 4/2004 | Ball et al. | 623/19.14 |
| 2004/0143336 A1 | 7/2004 | Burkinshaw | |
| 2004/0143337 A1 | 7/2004 | Burkinshaw | |
| 2004/0186579 A1 | 9/2004 | Callaway et al. | |
| 2004/0210317 A1 | 10/2004 | Maroney et al. | |
| 2004/0220673 A1* | 11/2004 | Pria | 623/19.12 |
| 2004/0220674 A1* | 11/2004 | Pria | 623/19.12 |
| 2004/0236428 A1 | 11/2004 | Burkinshaw et al. | |
| 2004/0267370 A1 | 12/2004 | Ondrla | |
| 2005/0033443 A1* | 2/2005 | Blatter et al. | 623/19.14 |
| 2005/0085921 A1 | 4/2005 | Gupta et al. | |
| 2005/0113931 A1 | 5/2005 | Horber | |
| 2005/0128755 A1 | 6/2005 | Matts et al. | |
| 2005/0137709 A1 | 6/2005 | Klotz et al. | |
| 2005/0143829 A1 | 6/2005 | Ondrla et al. | |
| 2005/0256583 A1* | 11/2005 | Bouttens et al. | 623/19.13 |
| 2005/0278030 A1 | 12/2005 | Tornier et al. | |
| 2005/0278032 A1 | 12/2005 | Tornier et al. | |
| 2005/0288681 A1 | 12/2005 | Klotz et al. | |
| 2005/0288791 A1* | 12/2005 | Tornier et al. | 623/19.13 |
| 2006/0004462 A1 | 1/2006 | Gupta | |
| 2006/0020344 A1* | 1/2006 | Shultz et al. | 623/19.12 |
| 2006/0030946 A1 | 2/2006 | Ball et al. | |
| 2006/0036329 A1 | 2/2006 | Webster et al. | |
| 2006/0052875 A1 | 3/2006 | Bernero et al. | |
| 2006/0069445 A1 | 3/2006 | Ondrla et al. | |
| 2006/0079963 A1* | 4/2006 | Hansen | 623/19.11 |
| 2006/0129247 A1 | 6/2006 | Brown et al. | |
| 2006/0142872 A1 | 6/2006 | Klotz et al. | |
| 2006/0161260 A1 | 7/2006 | Thomas et al. | |
| 2006/0200247 A1 | 9/2006 | Charrois | |
| 2006/0200248 A1 | 9/2006 | Beguin et al. | |
| 2006/0229730 A1 | 10/2006 | Railey et al. | |
| 2007/0050040 A1 | 3/2007 | Guederian et al. | |
| 2007/0078519 A1 | 4/2007 | Klotz | |
| 2007/0100458 A1* | 5/2007 | Dalla Pria | 623/19.13 |
| 2007/0112430 A1* | 5/2007 | Simmen et al. | 623/19.14 |
| 2007/0118230 A1* | 5/2007 | Callaway et al. | 623/23.47 |
| 2007/0156246 A1 | 7/2007 | Meswania et al. | |
| 2007/0173945 A1* | 7/2007 | Wiley et al. | 623/19.13 |
| 2007/0179624 A1* | 8/2007 | Stone et al. | 623/19.13 |
| 2007/0198094 A1* | 8/2007 | Berelsman et al. | 623/19.14 |
| 2007/0225820 A1 | 9/2007 | Thomas et al. | |
| 2007/0243045 A1 | 10/2007 | Gaska | |
| 2007/0244563 A1 | 10/2007 | Roche et al. | |
| 2007/0299527 A1* | 12/2007 | McCleary et al. | 623/18.11 |
| 2008/0221622 A1 | 9/2008 | Triplett et al. | |
| 2008/0228281 A1* | 9/2008 | Forrer et al. | 623/19.12 |
| 2008/0243261 A1 | 10/2008 | Wyss et al. | |
| 2008/0243262 A1 | 10/2008 | Lee | |
| 2008/0275507 A1 | 11/2008 | Triplett et al. | |
| 2008/0294268 A1 | 11/2008 | Baum et al. | |
| 2008/0306600 A1* | 12/2008 | Huebner | 623/19.11 |
| 2009/0062923 A1* | 3/2009 | Swanson | 623/19.13 |
| 2009/0099662 A1* | 4/2009 | Splieth et al. | 623/19.14 |
| 2009/0149961 A1* | 6/2009 | Dallmann | 623/19.11 |
| 2009/0164021 A1* | 6/2009 | Dallmann | 623/19.11 |
| 2009/0171462 A1* | 7/2009 | Poncet et al. | 623/19.12 |
| 2009/0192621 A1* | 7/2009 | Winslow et al. | 623/19.14 |
| 2009/0210065 A1* | 8/2009 | Nerot et al. | 623/19.14 |
| 2009/0216332 A1* | 8/2009 | Splieth et al. | 623/19.14 |
| 2009/0270993 A1* | 10/2009 | Maisonneuve et al. | 623/19.14 |
| 2009/0281630 A1* | 11/2009 | Delince et al. | 623/19.13 |
| 2009/0287309 A1* | 11/2009 | Walch et al. | 623/18.11 |
| 2010/0023068 A1 | 1/2010 | Bouttens et al. | |
| 2010/0049327 A1* | 2/2010 | Isch et al. | 623/19.12 |
| 2010/0057210 A1* | 3/2010 | Ondrla | 623/19.14 |
| 2010/0087927 A1* | 4/2010 | Roche et al. | 623/19.11 |
| 2010/0125336 A1* | 5/2010 | Johnson et al. | 623/19.14 |
| 2010/0161065 A1 | 6/2010 | Williams, Jr. et al. | |
| 2010/0161066 A1* | 6/2010 | Iannotti et al. | 623/19.11 |
| 2010/0211178 A1* | 8/2010 | Nogarin et al. | 623/19.14 |
| 2010/0222886 A1* | 9/2010 | Wiley et al. | 623/19.13 |
| 2010/0228352 A1 | 9/2010 | Courtney, Jr. et al. | |
| 2010/0234959 A1* | 9/2010 | Roche et al. | 623/19.13 |
| 2011/0054624 A1* | 3/2011 | Iannotti | 623/19.14 |
| 2011/0060417 A1* | 3/2011 | Simmen et al. | 623/19.11 |
| 2011/0082557 A1* | 4/2011 | Mutchler et al. | 623/19.14 |
| 2011/0098822 A1* | 4/2011 | Walch et al. | 623/19.13 |
| 2011/0106267 A1* | 5/2011 | Grant | 623/19.14 |
| 2011/0118846 A1* | 5/2011 | Katrana et al. | 623/19.13 |
| 2011/0153023 A1 | 6/2011 | Deffenbaugh et al. | |
| 2011/0178604 A1* | 7/2011 | Porter | 623/19.14 |
| 2011/0196491 A1 | 8/2011 | Huebner | |
| 2011/0295376 A1* | 12/2011 | Winslow | 623/19.14 |
| 2012/0029647 A1* | 2/2012 | Winslow et al. | 623/19.13 |
| 2012/0179262 A1* | 7/2012 | Metcalfe et al. | 623/19.14 |
| 2012/0191201 A1* | 7/2012 | Smits et al. | 623/19.11 |
| 2012/0209392 A1 | 8/2012 | Angibaud et al. | |
| 2012/0221112 A1 | 8/2012 | Lappin | |
| 2012/0253467 A1* | 10/2012 | Frankle | 623/19.11 |
| 2012/0259334 A1* | 10/2012 | Splieth et al. | 606/63 |
| 2012/0265315 A1* | 10/2012 | Kusogullari et al. | 623/19.14 |
| 2012/0271425 A1* | 10/2012 | Maurer | 623/19.12 |
| 2012/0271426 A1* | 10/2012 | Roche et al. | 623/19.13 |
| 2012/0277880 A1* | 11/2012 | Winslow et al. | 623/19.11 |
| 2012/0303130 A1* | 11/2012 | Winslow et al. | 623/19.12 |
| 2012/0330428 A1* | 12/2012 | Splieth et al. | 623/19.14 |
| 2013/0006369 A1* | 1/2013 | Wiley et al. | 623/19.14 |
| 2013/0197650 A1 | 8/2013 | Smits et al. | |
| 2013/0197651 A1 | 8/2013 | McDaniel et al. | |
| 2013/0197652 A1 | 8/2013 | Ekelund et al. | |
| 2013/0204375 A1* | 8/2013 | Winslow et al. | 623/19.13 |
| 2013/0245775 A1* | 9/2013 | Metcalfe, Nick | 623/19.12 |
| 2013/0261750 A1* | 10/2013 | Lappin | 623/19.11 |
| 2013/0267960 A1* | 10/2013 | Groh | 606/96 |
| 2013/0282129 A1* | 10/2013 | Phipps | 623/19.11 |
| 2013/0325130 A1* | 12/2013 | Viscardi et al. | 623/19.11 |
| 2013/0325131 A1* | 12/2013 | Roche et al. | 623/19.13 |
| 2013/0325133 A1* | 12/2013 | Viscardi et al. | 623/19.14 |
| 2013/0325134 A1* | 12/2013 | Viscardi et al. | 623/19.14 |

(56) References Cited

U.S. PATENT DOCUMENTS

| | | | |
|---|---|---|---|
| 2014/0018927 A1* | 1/2014 | De Wilde et al. | 623/19.11 |
| 2014/0039633 A1* | 2/2014 | Roche et al. | 623/19.13 |
| 2014/0039634 A1* | 2/2014 | Klotz | 623/19.14 |

FOREIGN PATENT DOCUMENTS

| | | | |
|---|---|---|---|
| EP | 1314407 | A1 | 5/2003 |
| EP | 1520560 | | 4/2005 |
| EP | 1656910 | A1 | 5/2006 |
| EP | 2047827 | A1 | 4/2009 |
| EP | 2201912 | A1 | 6/2010 |
| FR | 2689756 | | 10/1993 |
| FR | 2699400 | | 6/1994 |
| GB | 2001247 | A | 1/1979 |
| GB | 2405346 | A | 3/2005 |
| WO | 0147442 | A1 | 7/2001 |
| WO | 2005032430 | | 4/2005 |
| WO | 2007031575 | A1 | 3/2007 |
| WO | 2007039820 | | 4/2007 |
| WO | 2007084939 | | 7/2007 |
| WO | 2008000928 | A2 | 1/2008 |

OTHER PUBLICATIONS

Extended European Search Report for Application No. 12183703 dated Jan. 30, 2013.
Delta Reverse Shoulder System, Surgical Technique, DePuy 2004.
European Search Report, EP 10156704, dated Jun. 14, 2010.
Mode Operatoire, Operative Technique, Arrow, date not known.
Reverse Shoulder Prosthesis, Surgical Technique, Encore, 2005.
Trabecular Metal Reverse Shoulder System, Zimmer, date not known.
Extended European Search Report for Application No. EP13169019 dated Jul. 26, 2013.

* cited by examiner

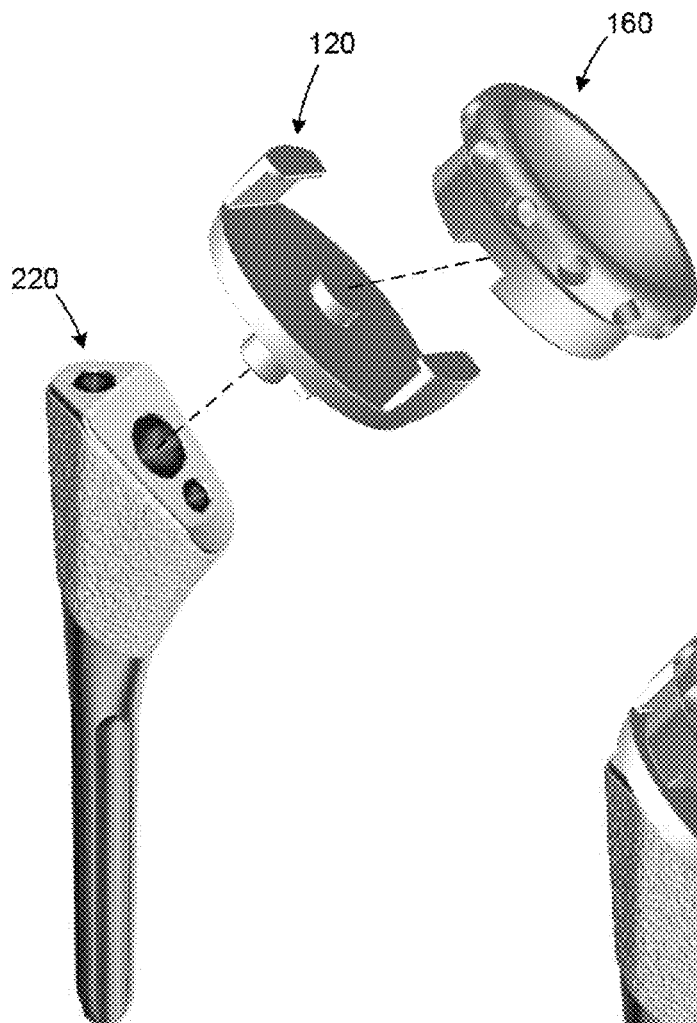
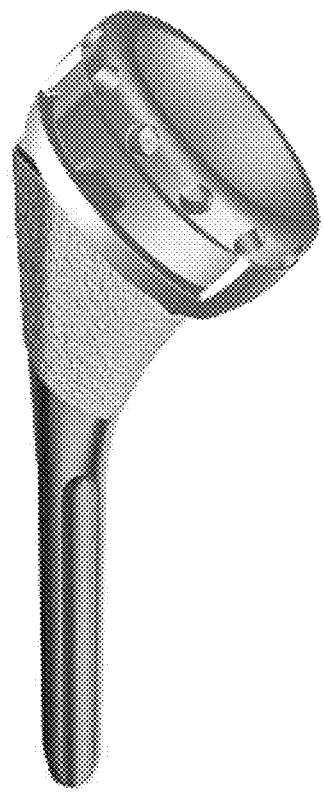
FIG. 9A
FIG. 9B

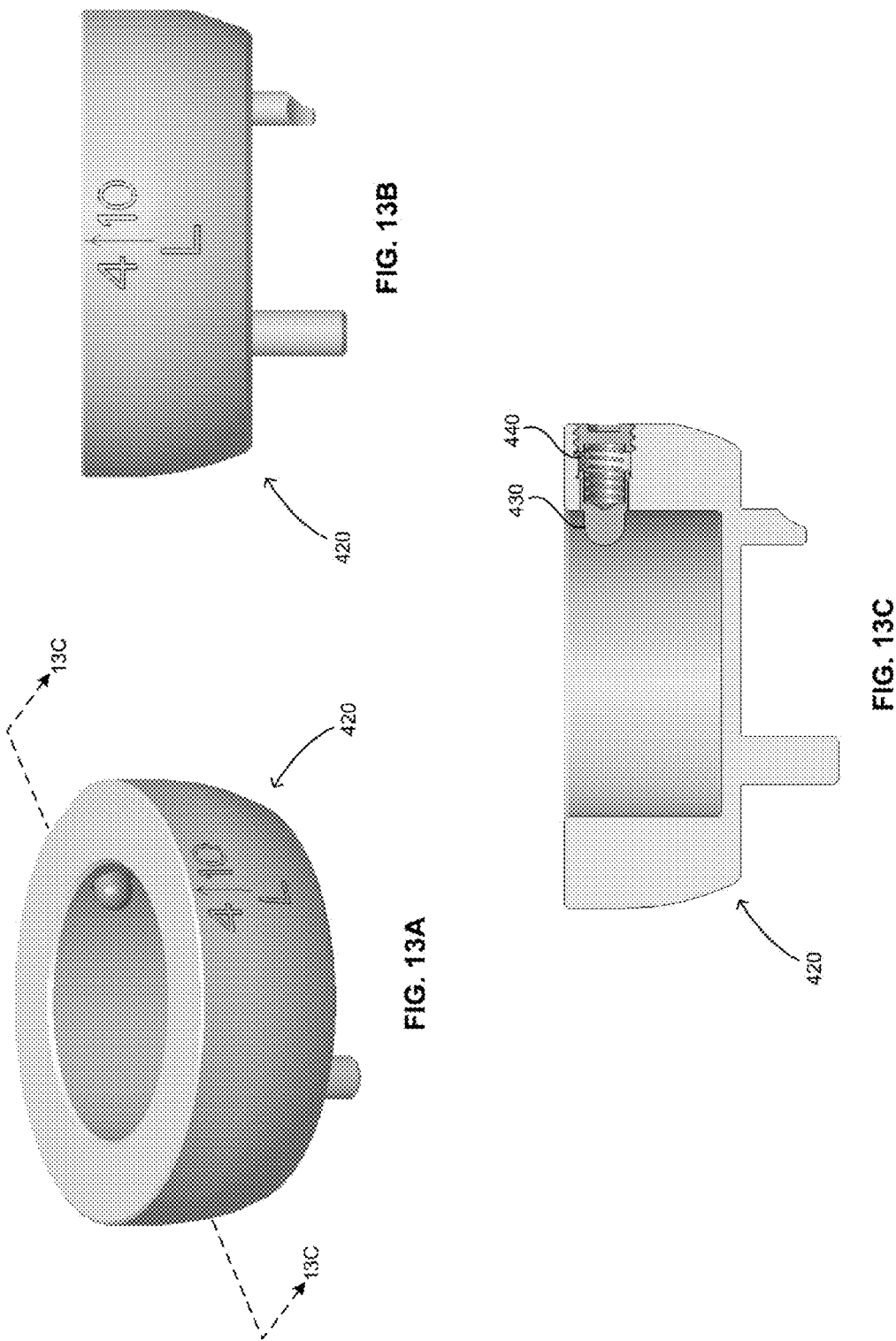

LATERAL ENTRY INSERT FOR CUP TRIAL

CROSS-REFERENCE TO RELATED APPLICATIONS

The present application is a continuation in part of U.S. patent application Ser. No. 13/484,557, filed May 31, 2012, the disclosure of which is incorporated herein by reference.

FIELD OF THE INVENTION

The present invention relates to a shoulder trial for reverse shoulder arthroplasty (RSA), and in particular it relates to such a trial including an insert and humeral cup that are configured to engage one another by sliding the insert from a transverse or lateral direction into engagement with the humeral cup.

BACKGROUND OF THE INVENTION

The successful outcome of RSA depends greatly on proper soft tissue tension in the shoulder joint. The stability of the shoulder joint is generally maintained from significant deltoid tension holding this ball and socket joint together. Some RSA systems require the surgeon to use a trial and error approach in establishing proper soft tissue tension. Such approaches often take several attempts before adequate stability is achieved.

When performing a trialing step in a reverse shoulder procedure, one important aspect is to determine the correct height of the humeral insert implant that will ultimately be chosen for the patient. A series of humeral insert trials with varying heights is normally utilized to determine the correct height for the implant. By using thicker or thinner insert trials the soft tissue tension and joint range of motion can be optimized for the patient.

Such trialing procedures generally include selecting a first trial insert, installing it into other parts of the shoulder system, reducing the joint, and then checking the joint for soft tissue tension and range of motion. The joint is then dislocated, and if the correct humeral insert implant height has been determined the reverse shoulder implantation proceeds. When the correct trial is determined, the soft tissue tension is significant, requiring the surgeon to apply extreme force to the humerus and surrounding soft tissues to reduce the joint. If no additional damage is done during this reduction process, the joint must then be dislocated to allow the surgeon to implant a joint replacement prosthesis.

If the correct humeral insert height has not yet been determined, then a second trial insert with a different thickness than the first trial is selected. The second trial insert is installed and the joint is assessed. As a result of the trialing procedure, the reverse shoulder joint can be reduced and dislocated multiple times.

Traditionally, each time the reverse shoulder joint is reduced and dislocated, the soft tissue has to be stretched in order for the glenosphere to be placed in or removed from the humeral insert. This stretching of the soft tissue can lead to joint instability and increased recovery time for the patient.

BRIEF SUMMARY OF THE INVENTION

The trial assembly of the present invention includes at least a trial cup and a trial insert. In one embodiment of the present invention, a recess or guide track of an insert trial is slid over a centering member or positive stop pin on a cup trial. Flanges on the cup trial are received within a groove of the insert trial as the guide track is slid over the centering member. After the centering member is located adjacent the deepest part of the guide track, the insert trial is preferably rotated in either a clockwise or counterclockwise direction substantially locking the lateral and vertical movement of the insert trial with respect to the cup trial. The rotational movement of the insert trial with respect to the cup trial can still occur.

The lateral engagement and disengagement of the insert trial and insert cup allows any size insert trial and cup to be used during the trialing process in contrast to having to reduce and distract the trials from each other prior to and after use.

In the past, there have been issues with achieving appropriate tensioning during RSA due to difficulties in inserting and removing the trials from between the humeral components and the glenosphere component on the glenoid. The trial assembly of the present invention provides a way of reducing and dislocating the joint without any temporary increase in joint tension that is usually experienced when reducing the ball up, over, and into the insert trial socket.

In accordance with a first aspect of the present invention is a trial assembly comprising a trial cup and a trial insert. The trial cup has a distal end surface and a proximal end surface, the proximal end surface including first and second flanges and a centering member protruding outwardly therefrom. The trial insert includes a proximal end portion and a shaft portion having a distal end, the shaft portion having a groove around an outer circumference thereof and a recess in the distal end thereof. The trial insert is operatively coupled to the trial cup when the centering member is received in the recess of the trial insert and an engagement member on each of the first and second flanges is received within the groove of the trial insert.

In one embodiment of this first aspect, the trial assembly further includes an elongated shaft having proximal and distal ends, the distal end surface of the trial cup adapted to lie adjacent to the proximal end of the elongated shaft when the trial cup is coupled to the elongated shaft.

In another embodiment of this first aspect, the first and second flanges of the trial cup extend outwardly from at least a portion of an outer circumference of the proximal end surface of the trial cup.

In yet another embodiment of this first aspect, the recess of the trial insert begins at the outer circumference of the shaft portion and terminates adjacent a central axis of the trial insert. When a longitudinal axis of the centering member is collinear with the central axis of the trial insert, the trial insert may be rotated in a radial direction about the central axis thereof. Further, rotating the trial insert 90° in either a first or second radial direction about a central axis thereof results in lateral locking of the trial insert and trial cup such that the trial insert and trial cup cannot be uncoupled by offsetting the longitudinal axis of the centering member of the trial cup and central axis of the trial insert. Further still, rotating the trial insert another 90° in either a first or second radial direction about the central axis thereof results in lateral unlocking of the trial insert and trial cup such that the trial insert and trial cup can be uncoupled by offsetting the longitudinal axis of the centering member of the trial cup and central axis of the trial insert.

In still yet another embodiment of this first aspect, the proximal end portion of the trial insert has a concave recess therein.

In still yet another embodiment of this first aspect, the proximal end portion of the insert includes an outer face having a plurality of calibration marks arranged thereon. The calibration marks are preferably located at 90° increments.

In still yet another embodiment of this first aspect, an outer face of the insert includes a plurality of attachment locations adapted to be engaged by an adjustment tool for rotating the trial insert about the central axis thereof.

In still yet another embodiment of this first aspect, the proximal end surface of the cup has a marker thereon.

In still yet another embodiment of this first aspect, a size or height of the trial assembly is measured by the axial distance between a proximal end surface of the trial insert and the distal end surface of the trial cup.

In accordance with a second aspect of the present invention is a trial assembly comprising a trial cup and a trial insert. The trial cup has a distal end surface and a proximal end surface, the proximal end surface including first and second flanges about a circumference thereof and a centering member protruding outwardly along a central longitudinal axis thereof. The trial insert includes a proximal end portion and a shaft portion having a distal end, the shaft portion having a groove around an outer circumference thereof and a recess in the distal end thereof, the recess begins about a circumference of the shaft and terminates adjacent a central longitudinal axis of the trial insert. The trial insert is operatively coupled to the trial cup when the centering member is received in the recess of the trial insert such that the central longitudinal axes of the centering member and trial insert are collinear and a portion of each of the first and second flanges is received at least partially within the groove of the trial insert.

In one embodiment of this second aspect, when the central longitudinal axes of the centering member and trial insert are collinear, the trial insert may be rotated in a radial direction about the central longitudinal axis of the centering member. Further, rotating the trial insert 90° in either a first or second radial direction about a central axis thereof results in lateral locking of the trial insert and trial cup such that the trial insert and trial cup cannot be uncoupled by offsetting the longitudinal axis of the centering member of the trial cup and central axis of the trial insert. Further still, rotating the trial insert another 90° in either a first or second radial direction about the central axis thereof results in lateral unlocking of the trial insert and trial cup such that the trial insert and trial cup can be uncoupled by offsetting the longitudinal axis of the centering member of the trial cup and central axis of the trial insert.

In another embodiment of this second aspect, a size or height of the trial assembly is measured by the axial distance between a proximal end surface of the trial insert and the distal end surface of the trial cup.

In accordance with a third aspect of the present invention there is a trialing system in which a surgeon has five different trial options. The trialing system comprises at least one stem member having a shaft portion adapted to be received in a canal of a humeral bone of a patient. First and second trial cups and a prosthesis cup are each adapted to be coupled at a distal end thereof to the at least one stem member, the first trial cup having a base surface and a centering member protruding outwardly therefrom, and the second trial cup and prosthesis cup each having a proximal end surface including a recess therein. A first trial insert includes a proximal end portion and a shaft portion having a distal end, and a second trial insert includes a proximal end portion and a shaft portion having a distal end, the shaft portion having a recess in the distal end thereof. The shaft portion of the first trial insert is received at least partially within the recess of the second trial cup in order to couple the first trial insert and second trial cup. The centering member of the first trial cup is received in the recess in the distal end of the second trial insert in order to couple the first trial cup and second trial insert. The shaft portion of the second trial insert is received at least partially within the recess of the second trial cup in order to couple the second trial insert and second trial cup.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 9A is an exploded view of an implant stem, trial cup and trial insert.

FIG. 9B is an assembled view of the implant stem, trial cup and trial insert shown in FIG. 9A.

FIGS. 13A-C show another embodiment of a trial cup of the present invention having a spring actuated sliding pin.

DETAILED DESCRIPTION

Figure 1:
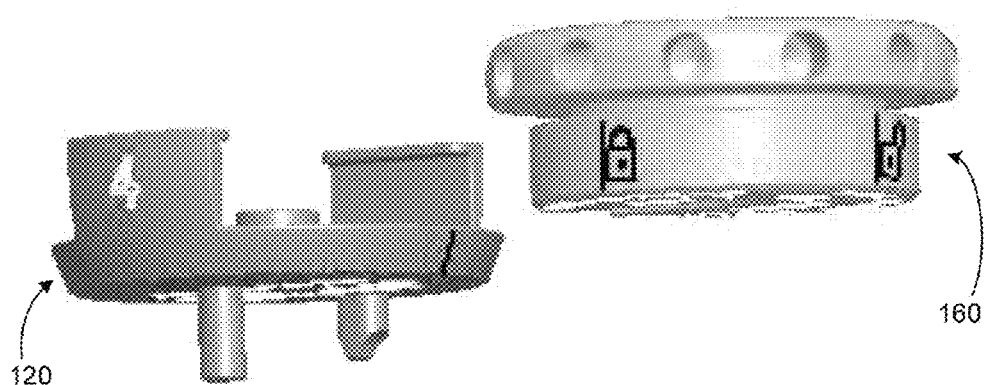
FIG. 1 is an exploded perspective view of one embodiment of a trial assembly of the present invention including a trial cup and a trial insert.
Figure 2:
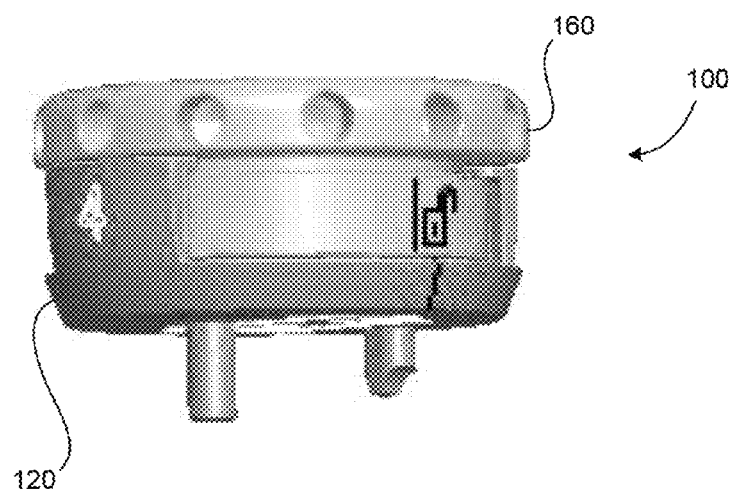
FIG. 2 is an assembled perspective view of one embodiment of a trial assembly of the present invention including the trial cup and the trial insert of FIG. 1.
Figure 3:
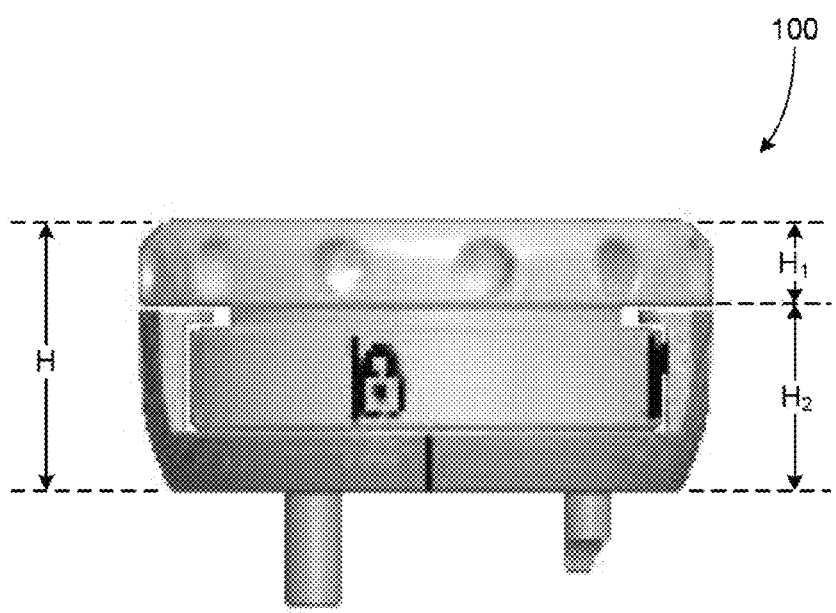
FIG. 3 is a side view of the trial assembly shown in FIG. 2.

Referring to FIGS. 1-3, there is shown an embodiment of a trial assembly of the present invention designated generally by reference numeral 100. As shown in those figures, trial assembly 100 includes a trial cup 120 and a trial insert 160.

Figure 4A:
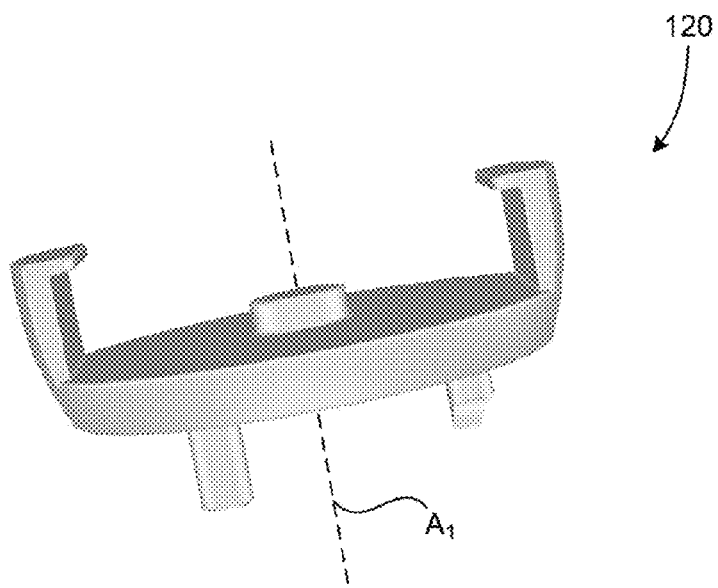
FIG. 4A is a perspective view of one embodiment of a trial cup of the present invention.
Figure 4B:
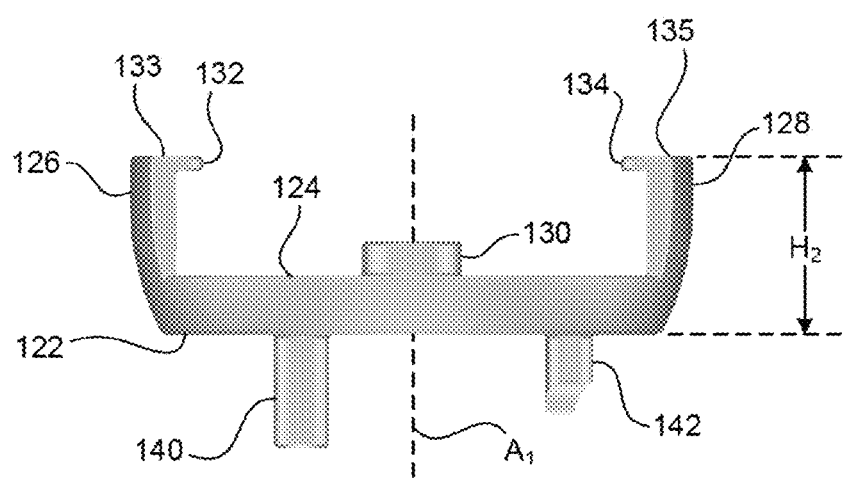
FIG. 4B is a side view of the trial cup shown in FIG. 4A.
Figure 4C:
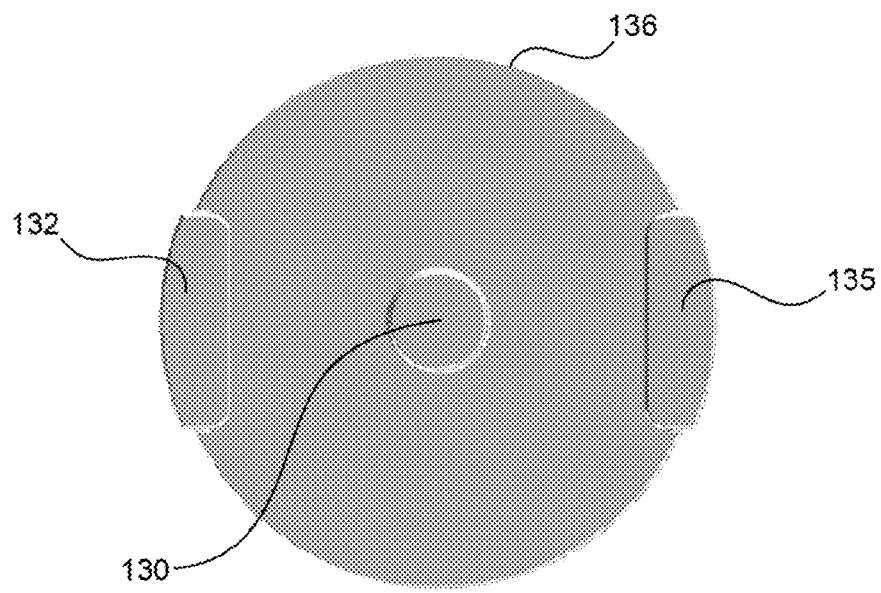
FIG. 4C is a top view of the trial cup shown in FIG. 4A.
Figure 4D:
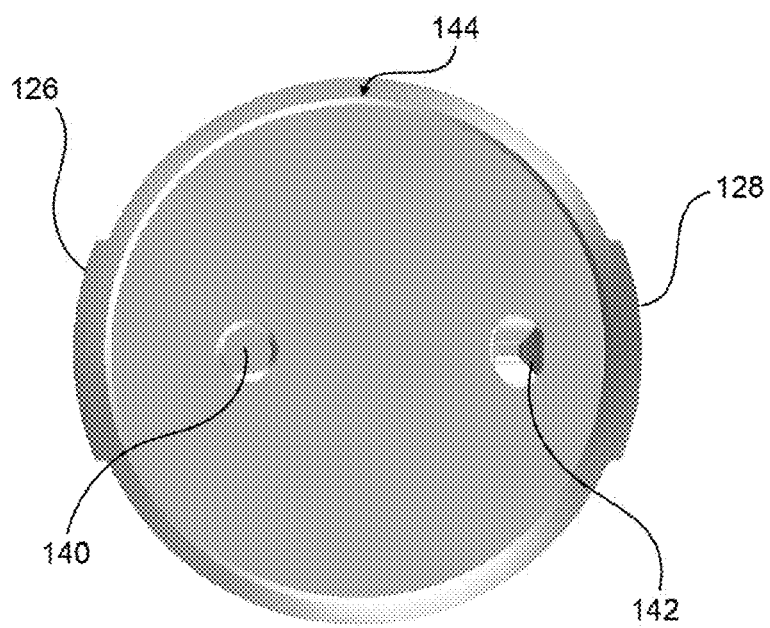
FIG. 4D is a bottom view of the trial cup shown in FIG. 4A.

FIGS. 4A-D show an embodiment of trial cup 120. As shown in these figures, trial cup 120 includes a distal end surface 122 and a base surface 124. Base surface 124 includes first and second flanges 126, 128 and a centering member 130 protruding outwardly therefrom. Base surface 124 preferably includes a marker 144 thereon as shown in FIG. 4D.

First and second flanges 126, 128 preferably extend outwardly from at least a portion of an outer circumference 136 of base surface 124 of trial cup 120. First and second flanges 126, 128 include an engagement member 132, 134 respectively. Engagement members 132, 134 preferably extend outwardly from inner surfaces of first and second flanges 126, 128. Engagement members 132, 134 preferably include a top surface 133, 135, respectively, which define a proximal end surface of trial cup 120. As seen in FIGS. 4A and 4B, axis A1 is a central longitudinal axis through centering member 130 and is also is a central longitudinal axis for trial cup 120.

Protruding outwardly from distal end surface 122 of trial cup are preferably first and second coupling members 140, 142. Coupling members 140, 142 are configured to engage first and second recesses in a stem or elongate shaft as shown in FIGS. 7A-B and 9A-B, for example, in order to couple the stem and trial cup 120.

FIGS. 5A-D show an embodiment of trial insert 160. As shown in these figures, trial insert 160 includes a proximal end portion 162 and a shaft portion 164 having a distal end 166. Shaft portion 164 has a groove 168 around an outer circumference 170 thereof and a recess 172 in the distal end 166 thereof. Recess 172 of trial insert 160 preferably begins at outer circumference 170 of shaft portion 164 and preferably terminates adjacent a central axis A2 of the trial insert 160.

Figure 5A:
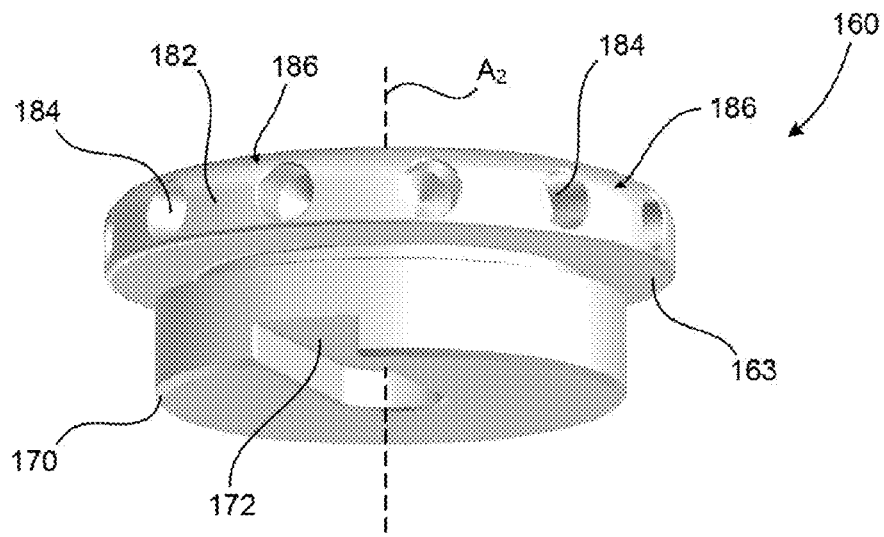
FIG. 5A is a perspective view of one embodiment of a trial insert of the present invention.
Figure 5B:
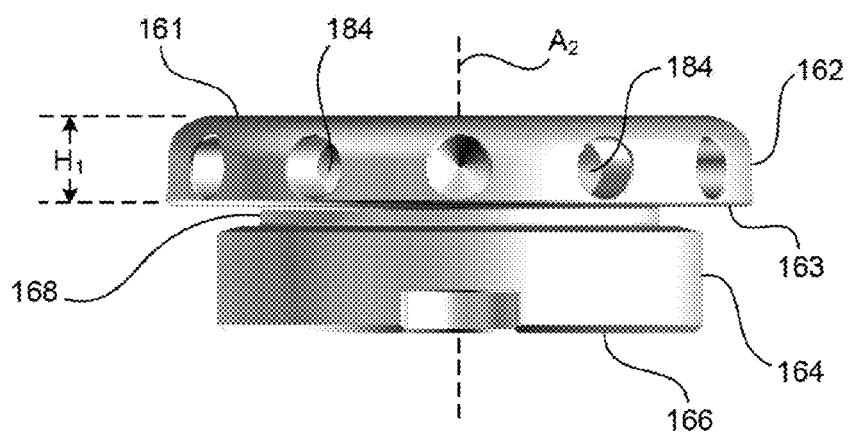
FIG. 5B is a side view of the trial insert shown in FIG. 5A.
Figure 5C:
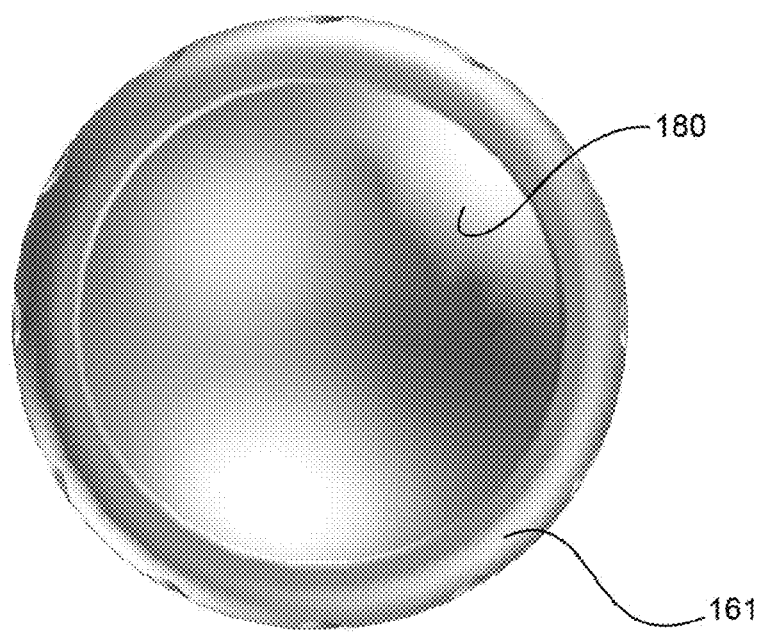
FIG. 5C is a top view of the trial insert shown in FIG. 5A.
Figure 5D:
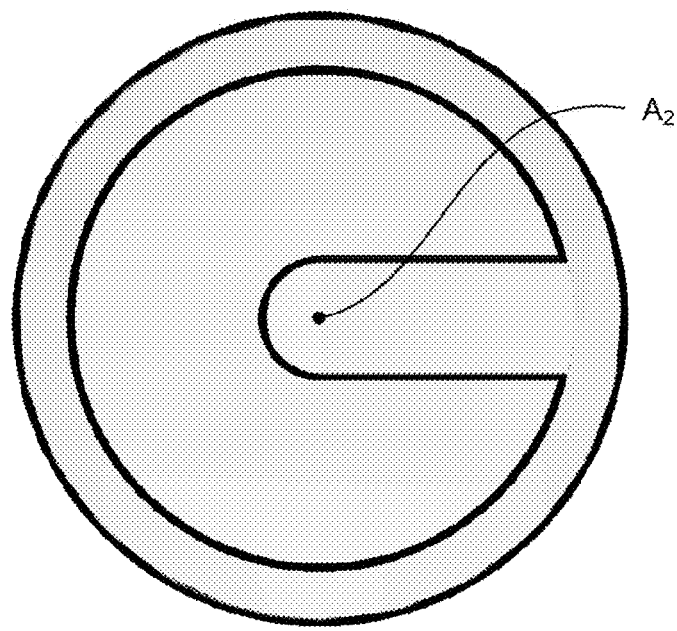
FIG. 5D is a bottom view of the trial insert shown in FIG. 5A.
Figure 5E:
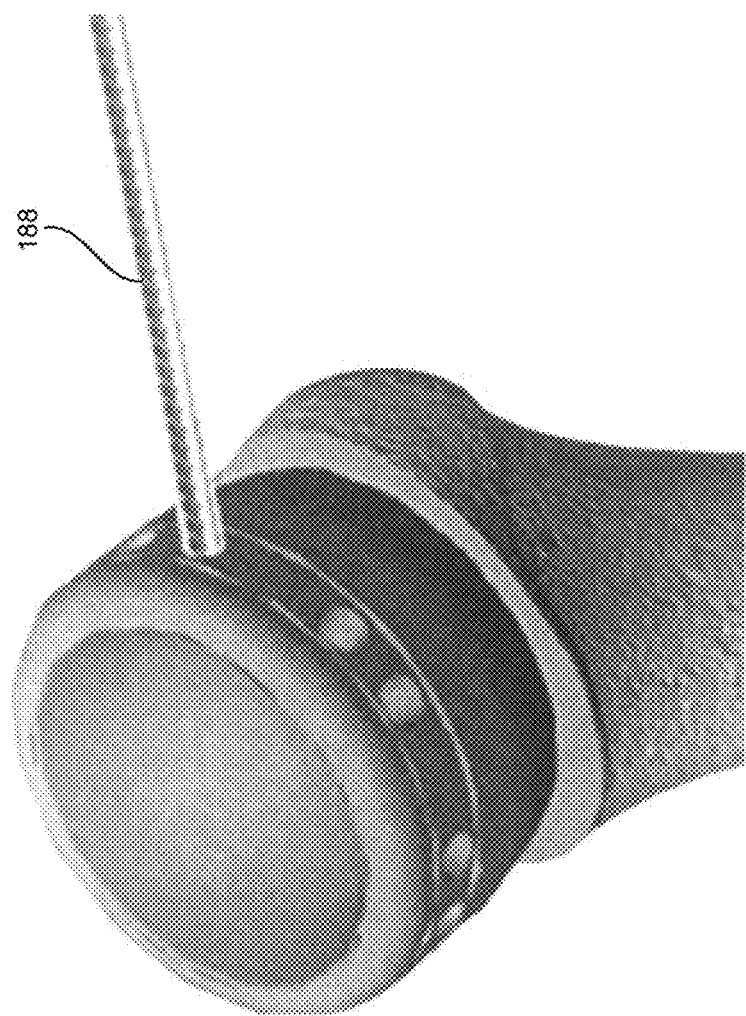
FIG. 5E shows an adjustment tool engaged to the trial insert shown in FIG. 5A.

As shown in FIG. 5C, proximal end portion 162 of trial insert 160 has a concave recess 180 therein. Concave recess 180 is adapted to contact and house a portion of a glenosphere (not shown). Proximal end portion 162 of trial insert 160 includes an outer face 182 preferably having a plurality of attachment locations 184 and calibration marks 186 arranged thereon. The attachment locations 184 are preferably located at 30° increments about outer face 182, but may be located from one another at increments greater or less than 30°. The calibration marks 186 are preferably located at 90° increments about outer face 182, but may be located from one another at increments greater or less than 90°. Attachment locations 184 are adapted to be engaged by an adjustment tool 188 as shown in FIG. 5E, for example, for rotating the trial insert 160 about central axis A2 thereof.

A reverse shoulder implant typically consists of five components: a humeral stem, a humeral cup, a humeral insert, a glenosphere baseplate, and a glenosphere. The embodiment of trial assembly 100 shown in FIGS. 1-3 includes two distinct components, namely trial cup 120 and trial insert 160, which are designed to allow a surgeon to determine which size humeral cup and humeral insert are needed to provide a shoulder joint with optimal deltoid tension in a RSA procedure. Both trial cup 120 and trial insert 160 are designed to work with other components or parts of a reverse shoulder implant and instrumentation thereof as part of a complete system in order to give a surgeon intraoperative flexibility and to accommodate surgeon preference. In addition, the design of trial cup 120 and trial insert 160 allows trial insert 160 to slide into trial cup 120 from a direction substantially transverse to the direction of trial cup axis A1, which minimizes soft tissue stretching when reducing or dislocating a reverse shoulder during a trialing process, and gives a surgeon the ability to perform a trialing procedure using instruments only or some combination of instruments and implants.

The design of trial assembly 100 overcomes the challenge of soft tissue stretching when reducing or dislocating a joint by allowing the trial humeral insert to slide into the trial humeral cup at an angle substantially transverse to the axis of the cup. Since the trial insert 160 can enter the trial cup 120 at a transverse angle to trial cup axis A1, reduction or dislocation of the joint can be achieved without the need to pull the glenosphere over the rim of trial insert 160. Soft tissue stretching is therefore minimized.

In one method of the present invention, trial insert 160 is operatively coupled to trial cup 120 when centering member 130 of trial cup 120 is received in recess 172 of trial insert 160 and an engagement member 132, 134 on each of first and second flanges 126, 128 of trial cup 120 is received within groove 168 of trial insert 160. When centering member 130 is located within recess 172 of trial insert 160 and longitudinal axis A1 of centering member 130 is collinear with central axis A2 of trial insert 160, trial insert 160 may be rotated in a radial direction about central axis A2 thereof. The trial insert 160 can be reversibly locked into the trial cup 120 simply by turning the trial insert 160 approximately degrees to approximately 165 degrees after initially engaging the trial insert 160 and trial cup 120. For example, after axes A1, A2 become collinearly oriented, rotating the trial insert 160 approximately 90° in either a first or second radial direction about central axis A2 thereof results in lateral locking of trial insert 160 and trial cup 120 such that trial insert 160 and trial cup 120 cannot be uncoupled by offsetting longitudinal axis A1 of the centering member 130 of trial cup 120 and central axis A2 of trial insert 160. Rotating trial insert 160 approximately another 90° in either a first or second radial direction about central axis A2 thereof results in lateral unlocking of trial insert 160 and trial cup 120 such that trial insert 160 and trial cup 120 can be uncoupled by offsetting longitudinal axis A1 of centering member 130 of trial cup 120 and central axis A2 of trial insert 160.

When operatively coupled, trial insert 160 can be rotated with respect to trial cup 120 by using an attachment tool having an end that can be received in attachment locations 184. A surgeon can estimate the amount of degrees that trial insert 160 has been rotated with respect to trial cup 120 by visualizing the movement of calibration marks 186 located on outer face 182 or by visualizing the movement of calibration marks 186 with respect to marker 144 located on base surface 124 of trial cup 120.

As shown in FIGS. 3 and 5B, a first height H1 is defined by the planar distance between a proximal end surface 161 and distal surface 163 of proximal end portion 162 of trial insert 160. As shown in FIGS. 3 and 4B, a second height H2 is defined by the planar distance between a top surface 133, 135 of engagement members 132, 134 and distal end surface 122 of trial cup 120. A size or height H of trial assembly 100 is measured by the axial or planar distance between proximal surface 161 of trial insert 160 and distal end surface 122 of trial cup 120 as shown in FIG. 3.

During the trial process, a surgeon may use one or more of a plurality of different sized trial cups and inserts. Each insert 160 preferably has a first height H1 between 4 mm and 12 mm in increments of 2 mm as shown in the chart below. A surgeon may then use one or more of a plurality of different sized trial cups 120. Each cup 120 preferably has a second height H2 that is either 4 mm or 10 mm as shown in the chart below. The following chart is a non-limiting example of the different sized trial inserts 160, trial cups 120 and the resultant total height H (8 mm, 10 mm, 12 mm, 14 mm, 16 mm, 18 mm, 20 mm and 22 mm) that can be achieved when trial inserts 160 and trial cups 120 are assembled and used during the trialing process:

|  | 4 mm Insert | 6 mm Insert | 8 mm Insert | 10 mm Insert | 12 mm Insert |
| --- | --- | --- | --- | --- | --- |
| 4 mm Cup | 8 | 10 | 12 | 14 | 16 |
| 10 mm Cup | 14 | 16 | 18 | 20 | 22 |

Figure 6B:
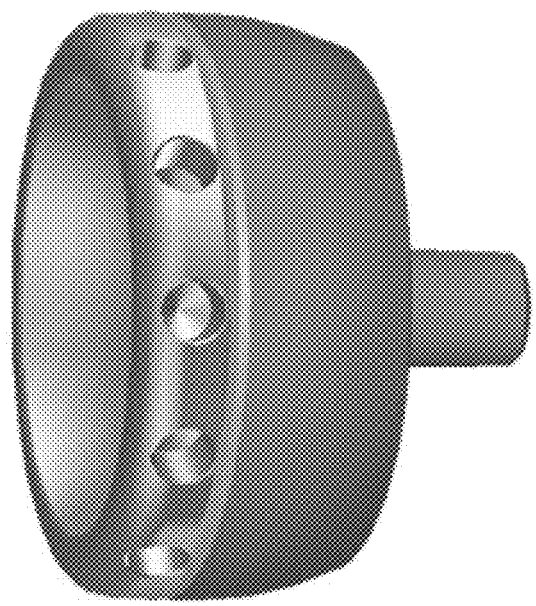
FIG. 6B is an assembled view of the implant cup and trial insert shown in FIG. 6A.
Figure 6A:
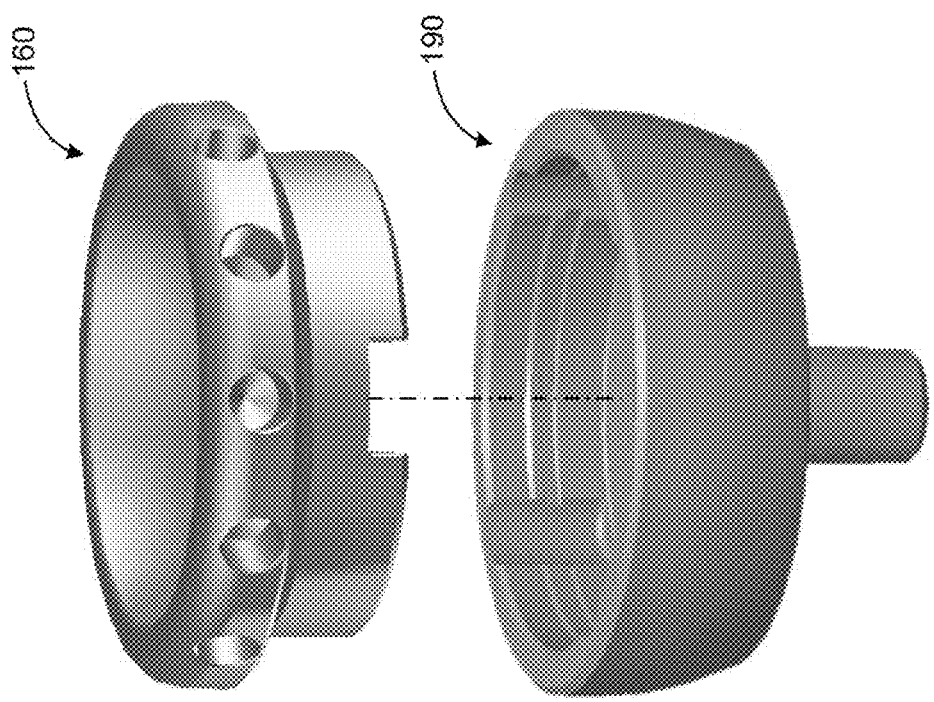
FIG. 6A is an exploded view of an implant cup and trial insert.
Figures 7A, 7B:
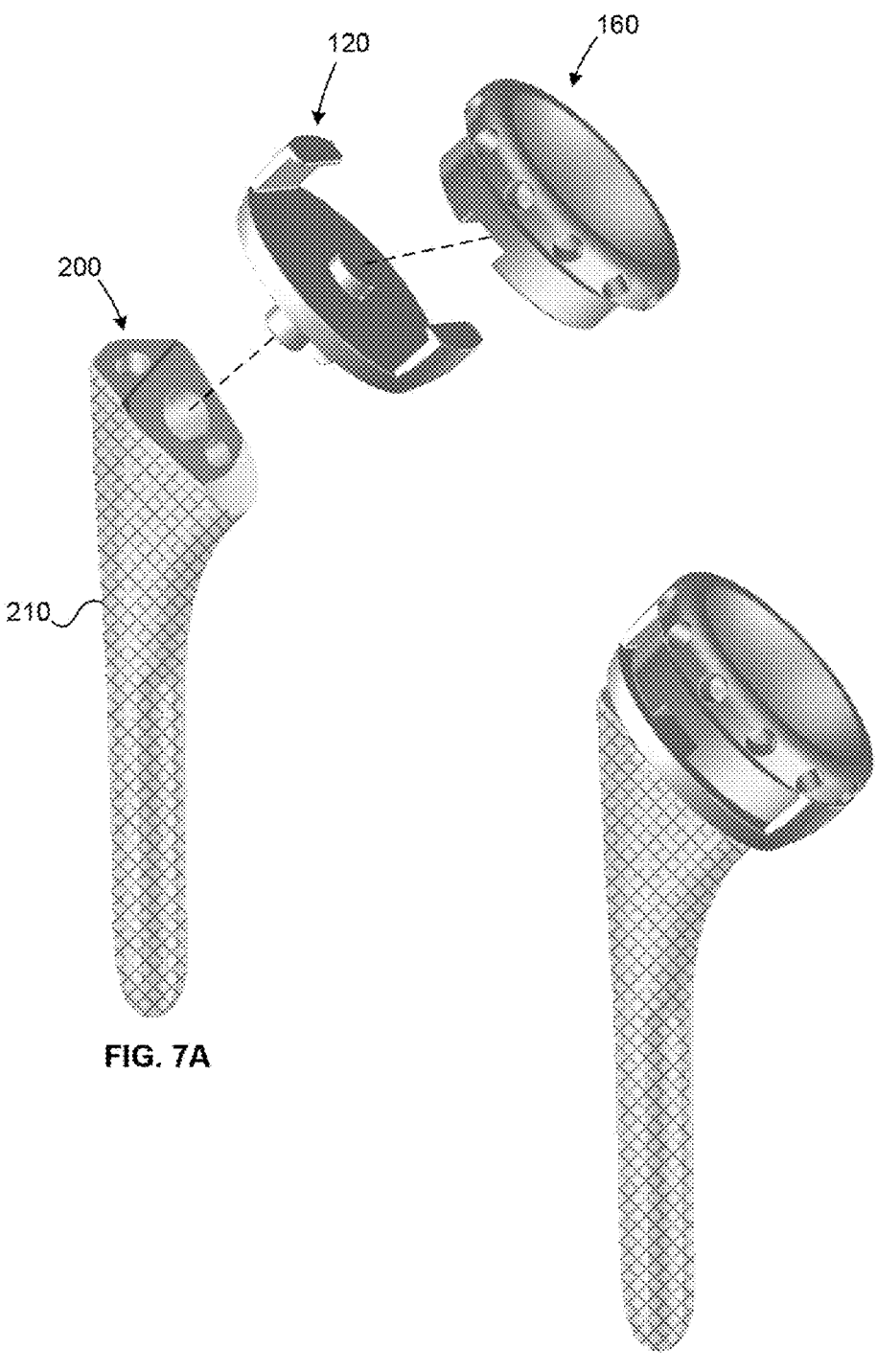
FIG. 7A is an exploded view of a broach, trial cup and trial insert.
FIG. 7B is an assembled view of the broach, cup and trial insert shown in FIG. 7A.

The design of trial assembly 100 overcomes the challenge of having one system allowing multiple intraoperative options with regard to trialing by allowing the trial cup 120 to be connected to either a broach 200 as shown in FIGS. 7A-B or humeral stem implant 220 as shown in FIGS. 9A-B, and also by allowing the trial insert 160 to be able to be connected to either trial cup 120 or implant cup 190 as shown in FIGS. 6A-6B and 8A-8B.

Surgeon preferences result in implants and instruments being used in different combinations. For example, some surgeons prefer to perform the trialing procedure off of a broach including cutting portions 210 such as teeth, for example, as shown in FIGS. 7A-7B used to create a cavity into which a humeral stem implant will eventually be placed. Some surgeons instead prefer to trial off of the humeral stem itself as shown in FIGS. 8A-8B and 9A-9B. As a result, it is advantageous for any trial humeral cup to be able to be connected to both the broach and humeral stem implant. Likewise, some surgeons prefer to perform the trialing procedure off of a trial humeral cup and some surgeons prefer to trial off of the humeral cup implant. Therefore it is advantageous for the humeral insert trial to be able to be connected to both the trial humeral cup and the humeral cup implant.

The same trial insert 160 that can be slid into engagement with trial cup 120 at an angle transverse to trial cup axis A1 and can also be dropped into a humeral cup implant along an axis coincident with both the humeral cup implant and trial insert 160. The attachment mechanisms that permit a connection between an implant component and a trial do not compromise the integrity of the attachment mechanisms used to connect two implant components. Such a design allows a surgeon to trial off of an implant with confidence that the trialing procedure is not damaging the implant attachment mechanisms which could possibly compromise the performance of the implant after final assembly.

In other embodiments, trial insert 160 may be able to engage trial cup 120 by sliding in a lateral direction into engagement with the trial cup 120, with trialing occurring as the trial insert 160 expands away from and collapses toward trial cup 120. For example, groove 168 of trial insert 160 may be in the form of a helical groove about shaft portion 164. The motion of trial insert along axis A1 of trial cup 120 may be guided by the interaction between the helical groove and an engagement member 133 or 125, for example. In such an embodiment, centering member 130 of trial cup 120 will have a larger height and recess 172 of trial insert 160 will have a greater depth such that the centering member 130 will remain at least partially within recess 172 as trial insert 160 expands and collapses with respect to trial cup 120.

The interaction of the helical groove and engagement member occurs much like that shown in U.S. Pat. No. 8,257,363 ("the '363 Patent") titled "Expandable Reverse Shoulder Trial," the disclosure of which is hereby incorporated by reference in its entirety. When trial insert 160 first becomes operatively engaged to trial cup 120, trial insert 160 may then be rotated into a fully collapsed or neutral position. Such a device may allow a surgeon to easily reduce the shoulder joint.

Preferably, trial insert 160 may then be advanced to a position where optimal deltoid tension is achieved. At this position, the trial insert 160 and trial cup 120 are preferably calibrated such that the surgeon may determine a liner thickness corresponding to a dialed position of the insert with respect to the cup.

Preferably, the surgeon may then easily collapse the trial back to the neutral position and simply dislocate the joint. Further, the trial may also be preferably expanded prior to joint reduction and collapsed prior to joint dislocation repeatedly, depending on surgeon preference. Once the trial has been optimized, a surgeon preferably records the dialed position of the expanded trial. This measurement should preferably be the liner thickness. If this measurement does not correspond to the size of a particular liner in the system, the surgeon may select a next larger sized liner. At this time, the surgeon may remove the trial and then implant a prosthesis including a humeral cup and the selected liner.

Figure 12A:
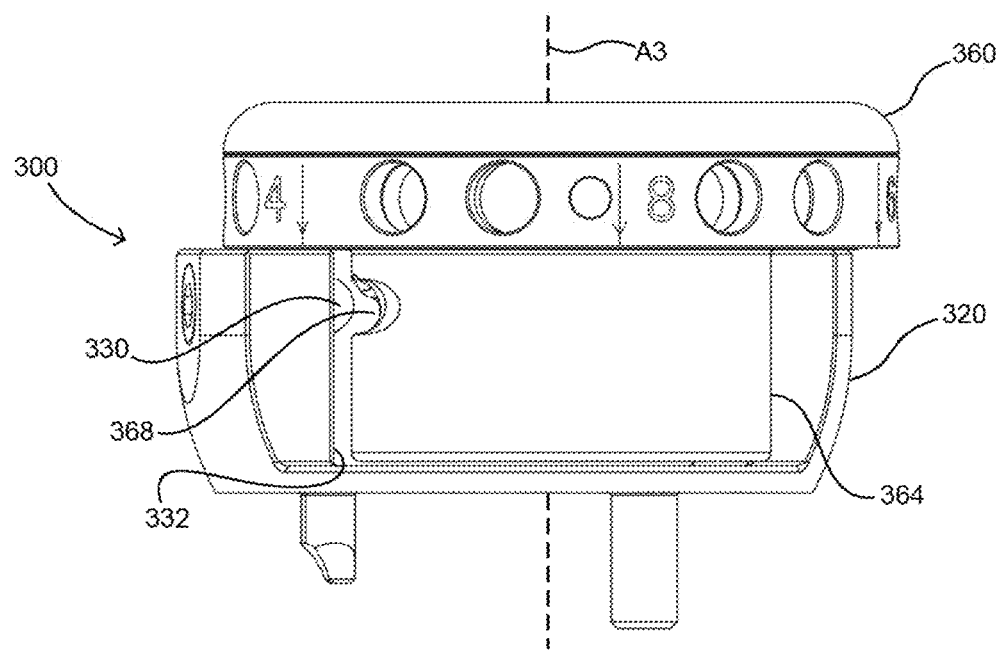
FIGS. 12A-C show another embodiment of an expandable trial of the present invention having a trial insert that is slidingly received by a trial cup, wherein the expandable trial expands and collapses by way of the interaction of a pin on the trial cup and a helical groove on the trial insert.
Figure 12B:
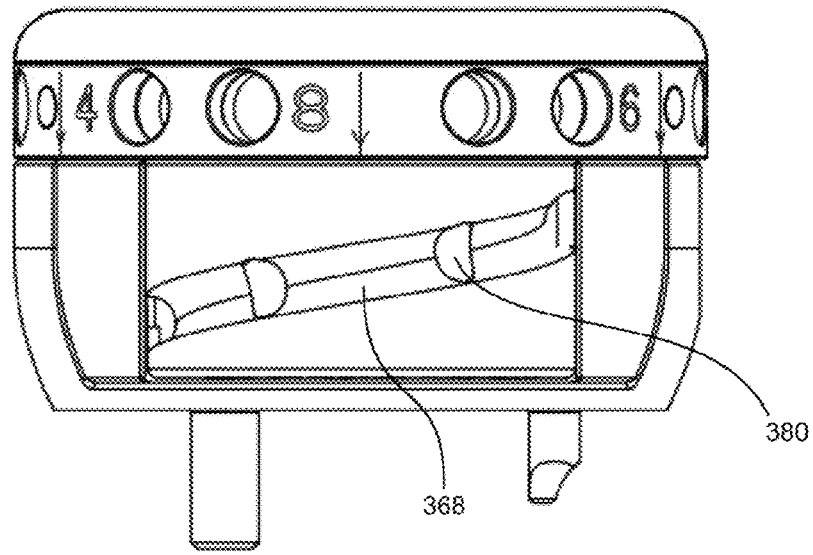
Figure 12C:
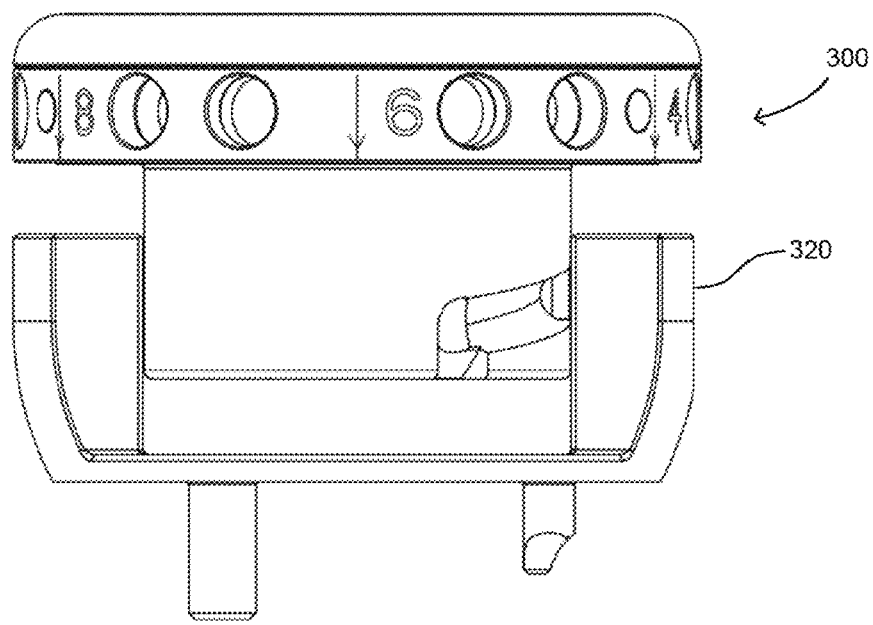
Figure 14A:
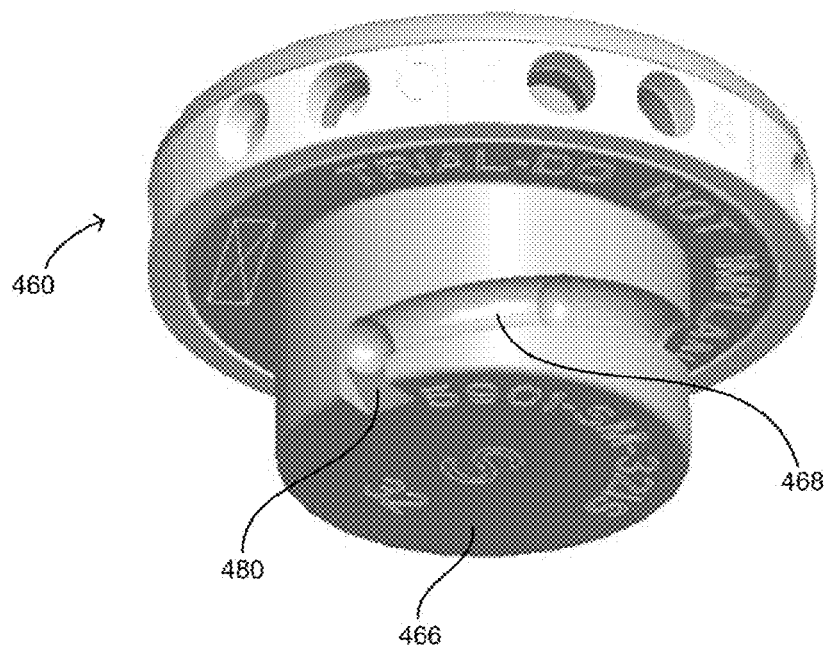
FIGS. 14A-B show another embodiment of a trial insert of the present invention having a helical groove wherein at one end thereof there is a lead-in slot.
Figure 14B:
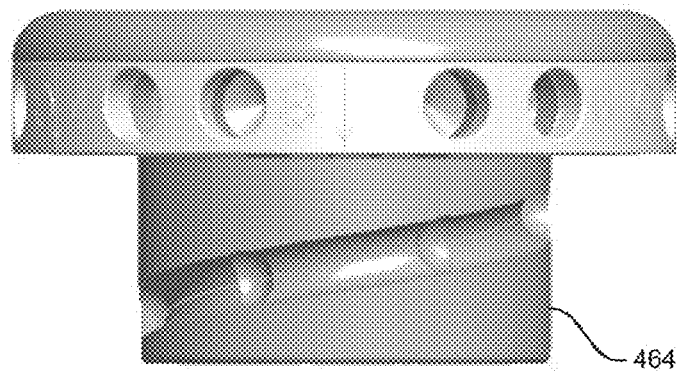

Another embodiment of such an expandable trial 300 is shown in FIGS. 12A-C. In this embodiment, trial insert 360 engages trial cup 320 by sliding in a lateral direction into engagement with the trial cup 320. A pin 330 extending outwardly from an inner wall 332 of trial cup 320 is received in a portion of a helical groove 368, with trialing occurring as trial insert 360 expands away from and collapses toward trial cup 320 via the interaction of pin 330 engaged to helical groove 368. For example, helical groove 368 of trial insert 360 may be formed about a shaft portion 364 of trial insert 360. The motion of trial insert 360 along an axis A3 of trial cup 120 may be guided by the interaction between the helical groove 368 and engagement member or pin 330.

FIG. 12B shows expandable trial 300 in a fully collapsed position while expandable trial 300 is shown in FIG. 12C in an expanded position with pin 330 being in engagement with one of a plurality of engagement recesses 380 formed along helical groove 368. Helical groove 368 preferably includes six engagement recesses 380, wherein the expandable trial 300 expands or collapses 1 mm as pin 330 engages an adjacent engagement recess 380 along helical groove 368. Helical groove 368 may include fewer or more than six engagement recesses 380 and the pitch of helical groove 368 may be such that expandable trial 300 expands or collapses more than or less than 1 mm as pin 330 engages an adjacent engagement recess 380 along helical groove 368.

Another embodiment of such an expandable trial 400 is shown in FIGS. 13A-15C. FIGS. 13A-C show one embodiment of a trial cup 420 having a spring actuated sliding pin 430 extending outwardly from an inner wall 432 of trial cup 420. FIGS. 14A-B show one embodiment of a trial insert 460 having a helical groove 468 having one end thereof adjacent a lead-in slot 480 located at a distal end 466 of a shaft portion 464 of insert trial 460. In this embodiment, trial insert 460 engages trial cup 420 when sliding pin 430 is received in lead-in slot 480 and onto helical groove 468. Sliding pin 430 extending outwardly from an inner wall 432 of trial cup 420 is received in a portion of a helical groove 468, with trialing occurring as trial insert 460 expands away from and collapses toward trial cup 420 via the interaction of pin 430 engaged to helical groove 468. The motion of trial insert 460 along a central longitudinal axis of trial cup 420 may be guided by the interaction between the helical groove 468 and engagement member or pin 430.

Figure 15A:
FIGS. 15A-C show another embodiment of an expandable trial of the present invention including trial cup as shown in FIGS. 13A-C and trial insert as shown in FIGS. 14A-B.

FIG. 15A shows lead-in slot 480 of trial insert 460 adjacent sliding pin 430 of trial insert 420 prior to sliding pin 430 being received in lead-in slot 480. FIG. 15C shows expandable trial 400 in a fully collapsed position while expandable trial 400 is shown in FIG. 15B in an expanded position with pin 430 being in engagement with one of a plurality of engagement recesses 480 formed along helical groove 468.

As described with respect to expandable trial 300, helical groove 468 of expandable trial 400 preferably includes six engagement recesses 480, wherein the expandable trial 400 expands or collapses 1 mm as pin 430 engages an adjacent engagement recess 480 along helical groove 468. Helical groove 468 may include fewer or more than six engagement recesses 480 and the pitch of helical groove 468 may be such that expandable trial 400 expands or collapses more than or less than 1 mm as pin 430 engages an adjacent engagement recess 480 along helical groove 468.

Figure 15B:
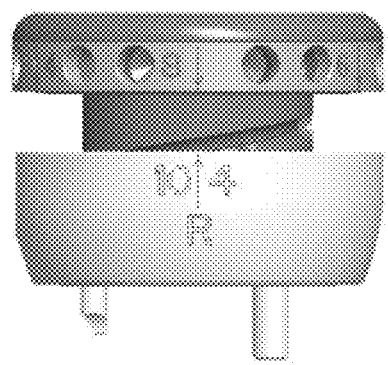
Figure 15C:
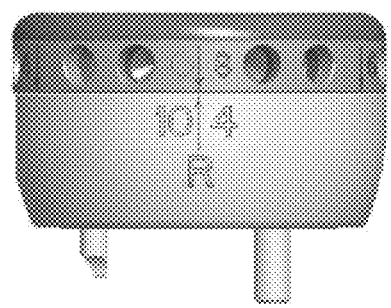
Figure 16A:
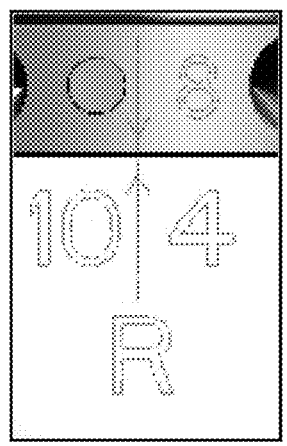
FIGS. 16A-B show the markings on the outer surfaces of the trial inserts and cup of the present invention shown in FIGS. 15C and 15B, respectively.
Figure 16B:
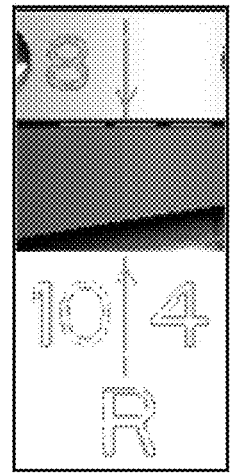

FIGS. 16A and 16B show examples of markings on the outer surfaces of the trial inserts and cup of the present invention shown in FIGS. 15C and 15B, respectively. The number "8" on the trial insert shown designates an example of the implant insert size. The numbers "10" and "4" on the trial cup shown designate an example of the implant cup size. Whichever number on the trial cup is on the same side as the trial insert is used to designate the fully collapsed assembly height. As shown in FIG. 16A, the fully collapsed assembly height is 12 mm, which includes a 4 mm trial cup and an 8 mm trial insert. As shown in FIG. 16B, the fully expanded assembly height is 18 mm, which includes a 10 mm trial cup and an 8 mm trial insert.

The embodiments described herein have applications in RSA as well as any other ball and socket joints that require dislocation and reduction, such as hip joints for example.

Figure 8A:
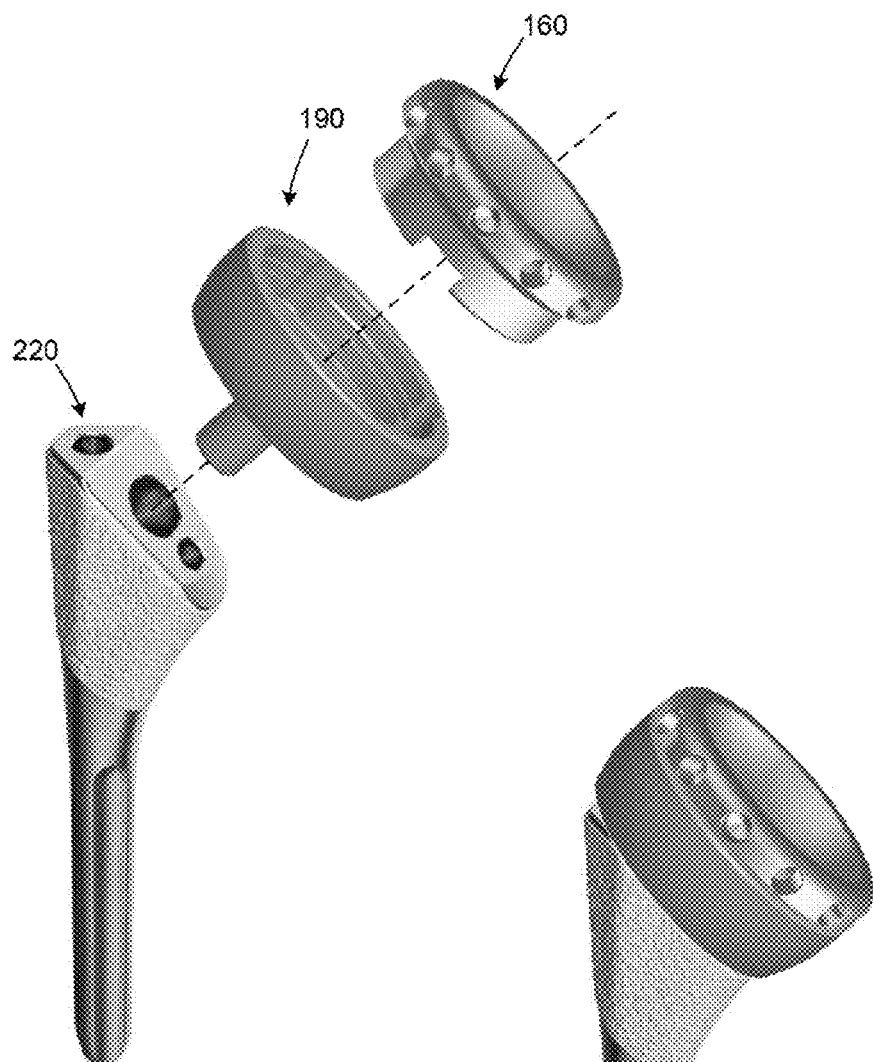
FIG. 8A is an exploded view of an implant stem, implant cup and trial insert.
Figure 8B:
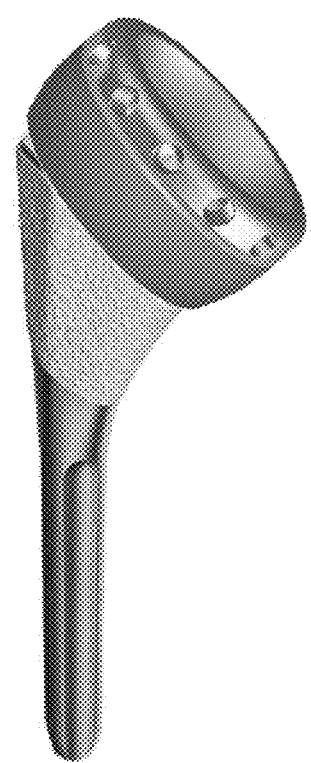
FIG. 8B is an assembled view of the implant stem, implant cup and trial insert shown in FIG. 8A.
Figure 10:
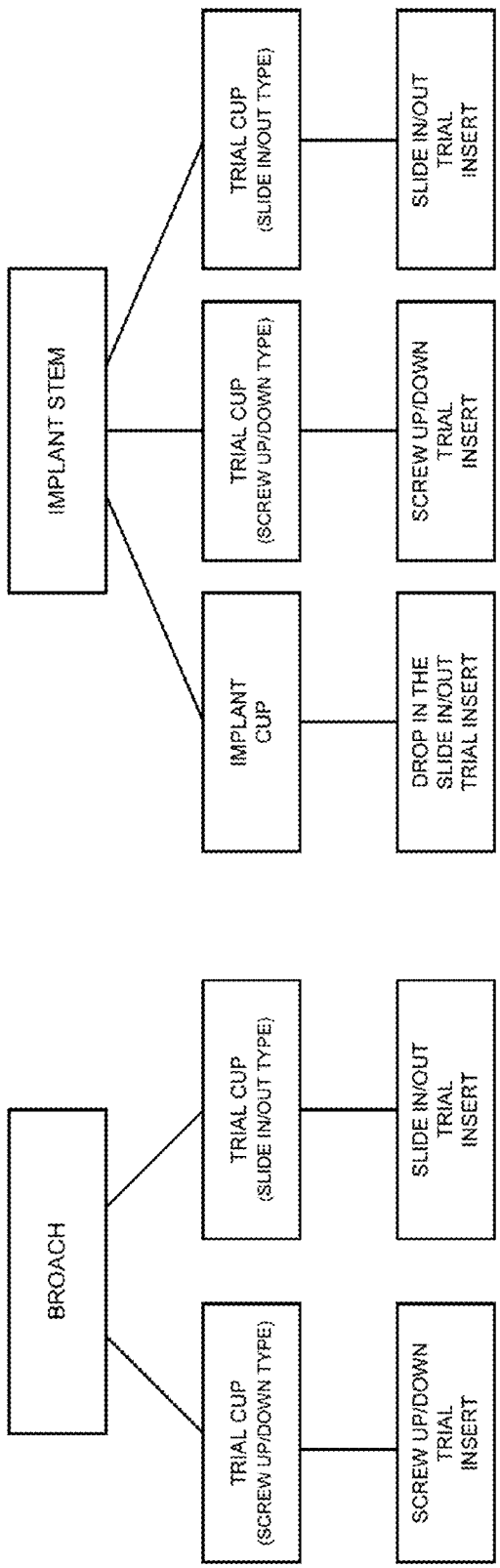
FIG. 10 is a flowchart showing two different trial options using a broach and three different trialing options using an implant stem.
Figure 11:
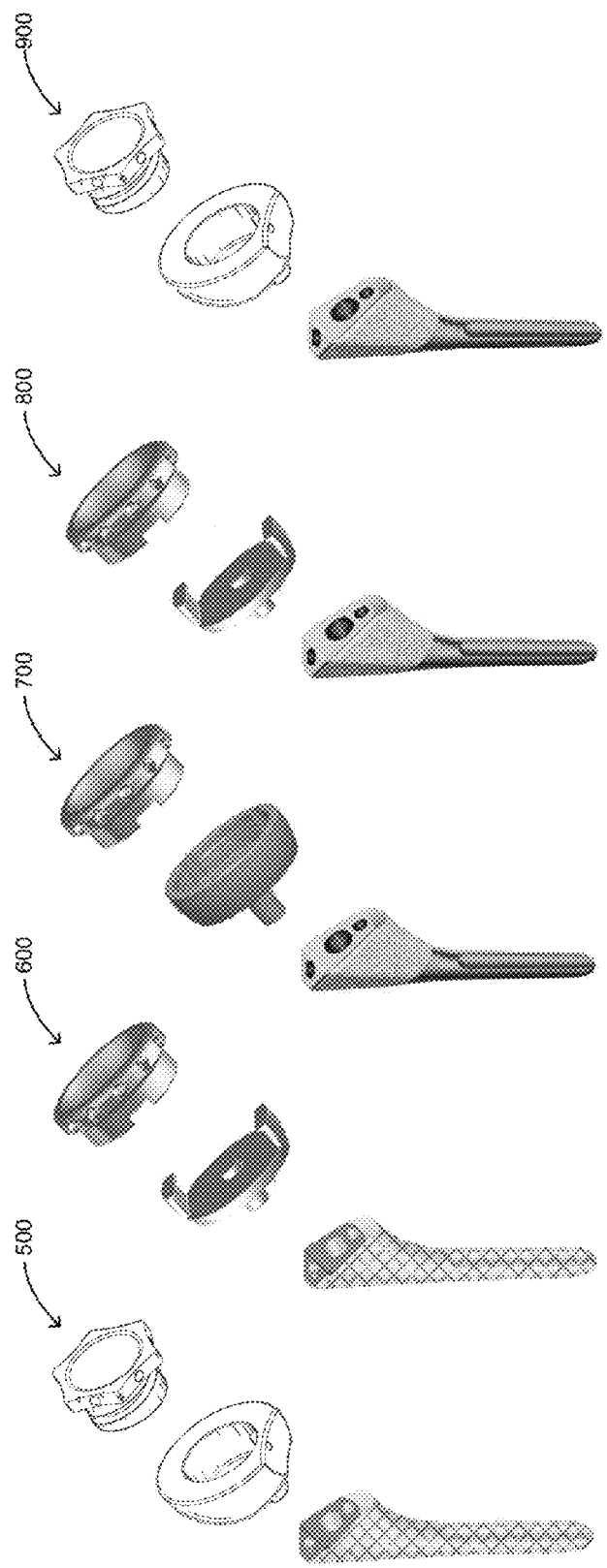
FIG. 11 shows five different trialing options using stem, cup and insert members of the present invention.

The aforementioned trial systems allow for trialing to occur off of a broach 200 as shown in FIGS. 7A-7B, for example, or off of an implant stem 220 as shown in FIGS. 8A-8B. FIG. 10 is a flowchart outlining the following five different trialing options that a surgeon may use in determining proper deltoid tension in a reverse shoulder procedure, for example, while FIG. 11 depicts each of these five different trial options wherein each option includes the use of a stem, cup and insert member. The five trialing options of FIGS. 10 and 11 are the following:

In a first trialing option 500, a type I trial cup such as shown in FIGS. 2A-2D of the '363 Patent, for example, is coupled to broach 200. A type I trial insert (screw up/down type) such as shown in FIG. 5A of the '363 Patent, for example, is coupled to the type I trial cup.

In a second trialing option 600, a type II trial cup 120 such as shown in FIGS. 4A-4D, for example, is coupled to broach 200. A type II trial insert 160 (slide in/out type) such as shown in FIG. 5A-5D, for example, is coupled to the type II trial cup.

In a third trialing option 700, an implant cup 190 such as shown in FIGS. 6A-6B, for example, is coupled to implant stem 220. A type II trial insert 160 such as shown in FIG. 5A-5D, for example, may be dropped in to implant cup 190 in order to coupled the type II trial insert 160 and implant cup 190.

In a forth trialing option 800, a type I trial cup such as shown in FIGS. 2A-2D of the '363 Patent, for example, is coupled to implant stem 220. A type I trial insert such as shown in FIG. 5A-5D of the '363 Patent, for example, is coupled to the type I trial cup.

In a fifth trialing option 900, a type II trial cup 120 such as shown in FIGS. 4A-4D, for example, is coupled to implant stem 220. A type II trial insert 160 such as shown in FIG. 5A-5D, for example, is coupled to the type II trial cup.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A trialing system comprising:
at least one stem member having a shaft portion adapted to be received in a canal of a humeral bone of a patient;
first and second trial cups and a prosthesis cup each adapted to be coupled at a distal end thereof to the at least one stem member, the first trial cup having a base surface and a centering member protruding outwardly therefrom, and the second trial cup and prosthesis cup each having a proximal end surface including a recess therein;
a first trial insert including a proximal end portion and a shaft portion having a distal end; and
a second trial insert including a proximal end portion and a shaft portion having a distal end, the shaft portion having a recess in the distal end thereof,
wherein the shaft portion of the first trial insert is received at least partially within the recess of the second trial cup in order to couple the first trial insert and second trial cup,
wherein the centering member of the first trial cup is received in the recess in the distal end of the second trial insert in order to couple the first trial cup and second trial insert, and
wherein the shaft portion of the second trial insert is received at least partially within the recess of the second trial cup in order to couple the second trial insert and second trial cup.

2. The trialing system of claim 1, wherein the at least one stem member is a broach.

3. The trialing system of claim 1, wherein the at least one stem member is a humeral implant.

4. The trialing system of claim 1, wherein the at least one stem member is a broach and a humeral implant.

5. The trialing system of claim 1, wherein the at least one stem member has a proximal end including an engagement member and the distal end of each of the first and second trial cups and prosthesis cup include an engagement member configured to engage to the engagement member of the at least one stem member in order to couple the at least one stem member to either the first trial cup, the second trial cup or the prosthesis cup.

6. The trialing system of claim 1, wherein the shaft portion of the first trial insert has a helical groove disposed on at least a portion thereof about an axis.

7. The trialing system of claim 6, wherein the recess of the second trial cup is defined by a circular wall, the circular wall having a guide pin protruding from the circular wall into the recess, the guide pin adapted to engage the helical groove of the shaft portion of the first trial insert such that the proximal end portion of the first trial insert may be linearly adjusted by rotating the trial insert in a first direction along a longitudinal axis of the second trial cup toward the proximal end portion of the second trial cup and in an opposite direction along the longitudinal axis of the second trial cup away from the proximal end portion of the second trial cup by the interaction of the guide pin and the groove.

8. The trialing system of claim 1, wherein the base surface of the first trial cup has first and second flanges protruding outwardly from at least a portion of an outer circumference thereof.

9. The trialing system of claim 8, wherein the shaft portion of the second trial insert has a groove around an outer circumference thereof.

10. The trialing system of claim 9, wherein the second trial insert is operatively coupled to the first trial cup when the centering member is received in the recess of the second trial insert and an engagement member on each of the first and second flanges of the first trial cup is received within the groove of the second trial insert.

11. The trialing system of claim 1, wherein the proximal end portions of both the first and second trial inserts have a concave recess portion.

12. A trialing system comprising:
first and second stem members each having a shaft portion adapted to be received in a canal of a humeral bone of a patient;
first and second trial cups and a prosthesis cup each adapted to be coupled at a distal end thereof to the either of the first and second stem members, the first trial cup having a base surface and a centering member protruding outwardly therefrom, and the second trial cup and prosthesis cup each having a proximal end surface including a recess therein;
a first trial insert including a proximal end portion and a shaft portion having a distal end; and
a second trial insert including a proximal end portion and a shaft portion having a distal end, the shaft portion having a recess in the distal end thereof,
wherein the shaft portion of the first trial insert is received at least partially within the recess of the second trial cup in order to couple the first trial insert and second trial cup,
wherein the centering member of the first trial cup is received in the recess in the distal end of the second trial insert in order to couple the first trial cup and second trial insert, and
wherein the shaft portion of the second trial insert is received at least partially within the recess of the second trial cup in order to couple the second trial insert and second trial cup.

13. The trialing system of claim 12, wherein the first stem member is a broach and the second stem member is a humeral implant.

14. The trialing system of claim 12, wherein the first and second stem members each have a proximal end including an engagement member, and the distal end of each of the first and second trial cups and prosthesis cup include an engagement member configured to engage to the engagement member of the first or second stem members in order to couple either the first of second stem member to either the first trial cup, the second trial cup or the prosthesis cup.

15. The trialing system of claim 12, wherein the shaft portion of the first trial insert has a helical groove disposed on at least a portion thereof about an axis.

16. The trialing system of claim 15, wherein the recess of the second trial cup is defined by a circular wall, the circular wall having a guide pin protruding from the circular wall into the recess, the guide pin adapted to engage the helical groove of the shaft portion of the first trial insert such that the proximal end portion of the first trial insert may be linearly adjusted by rotating the trial insert in a first direction along a longitudinal axis of the second trial cup toward the proximal end portion of the second trial cup and in an opposite direction along the longitudinal axis of the second trial cup away from the proximal end portion of the second trial cup by the interaction of the guide pin and the groove.

17. The trialing system of claim 12, wherein the base surface of the first trial cup has first and second flanges protruding outwardly from at least a portion of an outer circumference thereof.

18. The trialing system of claim 17, wherein the shaft portion of the second trial insert has a groove around an outer circumference thereof.

19. The trialing system of claim 18, wherein the second trial insert is operatively coupled to the first trial cup when the centering member is received in the recess of the second trial insert and an engagement member on each of the first and second flanges of the first trial cup is received within the groove of the second trial insert.

20. The trialing system of claim 12, wherein the proximal end portions of both the first and second trial inserts have a concave recess portion.

* * * * *